(12) United States Patent
Christensen et al.

(10) Patent No.: US 7,825,137 B2
(45) Date of Patent: Nov. 2, 2010

(54) METHOD OF TREATING ABNORMAL CELL GROWTH

(75) Inventors: James Gail Christensen, San Diego, CA (US); Yahong Zou, San Diego, CA (US)

(73) Assignee: Pfizer Inc., New York, NY (US)

( * ) Notice: Subject to any disclaimer, the term of this patent is extended or adjusted under 35 U.S.C. 154(b) by 170 days.

(21) Appl. No.: 12/095,114

(22) PCT Filed: Nov. 23, 2006

(86) PCT No.: PCT/IB2006/003397

§ 371 (c)(1),
(2), (4) Date: May 27, 2008

(87) PCT Pub. No.: WO2007/066187

PCT Pub. Date: Jun. 14, 2007

(65) Prior Publication Data

US 2008/0300273 A1    Dec. 4, 2008

Related U.S. Application Data

(60) Provisional application No. 60/742,766, filed on Dec. 5, 2005, provisional application No. 60/864,637, filed on Nov. 7, 2006.

(51) Int. Cl.
*A61K 31/454* (2006.01)
(52) U.S. Cl. .................................................. 514/318
(58) Field of Classification Search .................. 514/318
See application file for complete search history.

(56) References Cited

U.S. PATENT DOCUMENTS

| | | | |
|---|---|---|---|
| 6,313,137 | B1 | 11/2001 | Amin et al. |
| 6,498,165 | B1 | 12/2002 | Armstrong et al. |
| 6,825,198 | B2 | 11/2004 | Chiang et al. |
| 6,992,087 | B2 | 1/2006 | Verhoest et al. |
| 6,995,161 | B2 | 2/2006 | Yoon et al. |
| 7,205,408 | B2 | 4/2007 | Davies et al. |
| 7,230,098 | B2 | 6/2007 | Cui et al. |
| 2006/0046991 | A1 | 3/2006 | Cui et al. |
| 2006/0128724 | A1 | 6/2006 | Cui et al. |
| 2006/0178374 | A1 | 8/2006 | Cui et al. |
| 2007/0072874 | A1 | 3/2007 | Cui et al. |

FOREIGN PATENT DOCUMENTS

| | | |
|---|---|---|
| EP | 0 204 285 | 1/1992 |
| EP | 1 044 967 | 8/2004 |
| JP | 7 109260 | 4/1995 |
| WO | WO 93/15055 | 8/1993 |
| WO | WO 98/37080 | 8/1998 |
| WO | WO 99/55706 | 11/1999 |
| WO | 2006/021884 A2 * | 3/2006 |

OTHER PUBLICATIONS

Zou et al. Cancer Res., 2007, vol. 67, No. 9, pp. 4408-4417.*

Aebersold, D., et al., "Prevalence and clinical impact of Met Y1253D-activating point mutation in radiotherapy-treated squamous cell cancer of the oropharynx," *Oncogene*, 2003, 8519-8523, vol. 22, No. 52.

Bradbury H., et al., "New Non-Peptide Endothelin-A Receptor Antagonists: Synthesis, Biological Properties, and Structure-Activity Relationships of 5-(Dimethylamino)-N-pyridyl-, -N-pyrimidinyl-, -N-pyridazinyl-, and -N-pyrazinyl-1-naphthalenesulfonamides," *Journal of Medicinal Chemistry*, 1997, 996-1004, vol. 40, No. 6.

Bristol, J., et al., "An Improved Synthesis of 2-Amino-3-alkyloxypyridines by a Phase-Transfer Catalyzed Ether Synthesis," *Synthesis*, 1981, 971-973, vol. 12.

Christensen, J., et al., "c-Met as a target for human cancer and characterization of inhibitors for therapeutic intervention," *Cancer Letters*, 2005, 1-26, vol. 225, No. 1.

Dennin, F., et al., "Synthesis of Derivatives of Pyrazino[1,2-α]pyrimidin-4-ones," *Journal of Heterocyclic Chemistry*, 1990, 1639-1643, vol. 27.

Di Renzo, M., et al, "Overexpression and Amplification of the Met/HGF Receptor Gene during the Progression of Colorectal Cancer," *Clinical Cancer Research*, 1995, 147-154, vol. 1.

Di Renzo, M., et al., "Somatic mutations of the MET oncogene are selected during metastatic spread of human HNSC carcinomas," *Oncogene*, 2000, 1547-1555, vol. 19, No. 12.

Foks, H., et al, "Studies on Pyrazine Derivatives. XXX. Synthesis of Pyrazinylamino-1,3-Diazacycloalkanes of Potential Circulatory Activity," *Acta Poloniae Pharmaceutica*, 1997, 55-62, vol. 54, No. 1.

Gallego, M., et al., "Targeted expression of HGF/SF in mouse mammary epithelium leads to metastatic adenosquamous carcinomas through the activation of multiple signal transduction pathways," *Oncogene*, 2003, 8498-8508, vol. 22.

Gavezzotti, A., "Are Crystal Structures Predictable?," *Accounts of Chemical Research*, 1994, 309-314, vol. 27, No. 10.

Graveel, C., et al., "Tumorigenic Effects of Activating Met Mutations in a Knock-in Mouse Model," *Proceedings of the American Association for Cancer Research*, 2004, 5102, vol. 45.

Hanahan, D., et al., "The Hallmarks of Cancer," *Cell*, 2000, 57-70, vol. 100.

Hara, T., et al., "Amplification of c-myc, K-sam, and c-met in Gastric Cancers: Detection by Fluorescence in Situ Hybridization," *Laboratory Investigation*, 1998, 1143-1153, vol. 78, No. 9.

Kaminski, J., et al., "Antiulcer Agents. 2. Gastric Antisecretory, Cytoprotective, and Metabolic Properties of Substituted Imidazo[1,2-a]pyridines and Analogues," *Journal of Medicinal Chemistry*, 1987, 2031-2046, vol. 30, No. 11.

Jeffers, M., et al., "Activating mutations for the Met tyrosine kinase receptor in human cancer," *Proceedings of the National Academy of Science of the United States of America*, 1997, 11445-11450, vol. 94, No. 21.

(Continued)

*Primary Examiner*—James D Anderson
(74) *Attorney, Agent, or Firm*—Jeffrey H. Tidwell; Stephen D. Prodnuk; Vincent P. Liptak

(57) ABSTRACT

The present invention relates to the use of (R)-3-[1-(2,6-Dichloro-3-fluoro-phenyl)-ethoxy]-5-(1-piperidin-4-yl-1H-pyrazol-4-yl)-pyridin-2-ylamine, a novel c-Met/HGFR inhibitor, for treating abnormal cell growth in mammals. In particular, the invention provides methods of treating mammals suffering from cancer.

7 Claims, 11 Drawing Sheets

OTHER PUBLICATIONS

Jeffers, M., et al., "The mutationally activated Met receptor mediates motility and metastasis," *Proceedings of the National Academy of Science of the United States of America*, 1998, 14417-14422, vol. 95, No. 24.

Kuniyasu, H., et al., "Frequent Amplification of the *c-met* Gene in Scirrhous Type Stomach Cancer," *Biochemical and Biophysical Research Communications*, 1992, 227-232, vol. 189, No. 1.

Lee, J., et al., "A novel germ line juxtamembrane *Met* mutation in human gastric Cancer," *Oncogene*, 2000, 4947-4953, vol. 19.

Lorenzato, A., et al., "Novel Somatic Mutations of the *MET* Oncogene in Human Carcinoma Metastases Activating Cell Motility and Invasion," *Cancer Research*, 2002, 7025-7030, vol. 62, No. 23.

Ma, P., et al., "*c*-MET Expression/Activation, Functions, and Mutations in Non-small Cell Lung Cancer," *Proceedings of the American Association for Cancer Research*, 2004, 1875, vol. 45.

Ma, P., et al., "*c-Met* Mutational Analysis in Small Cell Lung Cancer: Novel Juxtamembrane Domain Mutations Regulating Cytoskeletal Functions," *Cancer Research*, 2003, 6272-6281, vol. 63, No. 19.

Otsuka, T., et al., "c-Met Autocrine Activation Induces Development of Malignant Melanoma and Acquisition of the Metastatic Phenotype," *Cancer Research*, 1998, 5157-5167, vol. 58, No. 22.

Park, W., et al., "Somatic Mutations in the Kinase Domain of the *Met*/Hepatocyte Growth Factor Receptor Gene in Childhood Hepatocellular Carcinomas," *Cancer Research*, 1999, 307-310, vol. 59, No. 2.

Pulford, K., et al., "Anaplastic Lymphoma Kinase Proteins in Growth Control and Cancer," *Journal of Cellular Physiology*, 2004, 330-358, vol. 199.

Schmidt, L., et al., "Germline and somatic mutations in the tyrosine kinase domain of the *MET* proto-oncogene in papillary renal carcinomas," *Nature Genetics*, 1997, 68-73, vol. 16, No. 1.

Schmidt, L., et al., "Novel mutations of the MET proto-oncogene in papillary renal carcinomas." *Oncogene*, 1999, 2343-2350, vol. 18, No. 14.

Schmidt, L., et al., "Two North American Families with Hereditary Papillary Renal Carcinoma and Identical Novel Mutations in the MET Proto-Oncogene," *Cancer Research*, 1998, 1719-1722, vol. 58, No. 8.

Shimomura, O., et al., "Semi-synthetic aequorins with improved sensitivity to Ca2+ ions," *Biochemical Journal*, 1989, 913-920, vol. 261.

Sollogoub, M., et al., "First synthesis of 1-deazacytidine, the C-nucleoside analogue of Cytidine," *Tetrahedron Letters*, 2002, 3121-3123, vol. 43.

Takayama, H., et al., "Diverse tumorigenesis associated with aberrant development in mice overexpressing hepatocyte growth factoryscatter factor," *Proceedings of the National Academy of Science of the United States of America*, 94, 701-706, vol. 94, No. 2.

Vippagunta, S., et al., "Crystalline Solids," *Advanced Drug Delivery Reviews*, 2001, 3-26, vol. 48.

Wan, W., et al., "Anaplastic lymphoma kinase activity is essential for the proliferation and survival of anaplastic large-cell lymphoma cells," *Blood*, 2006, 1617-1623, vol. 107, No. 4.

\* cited by examiner

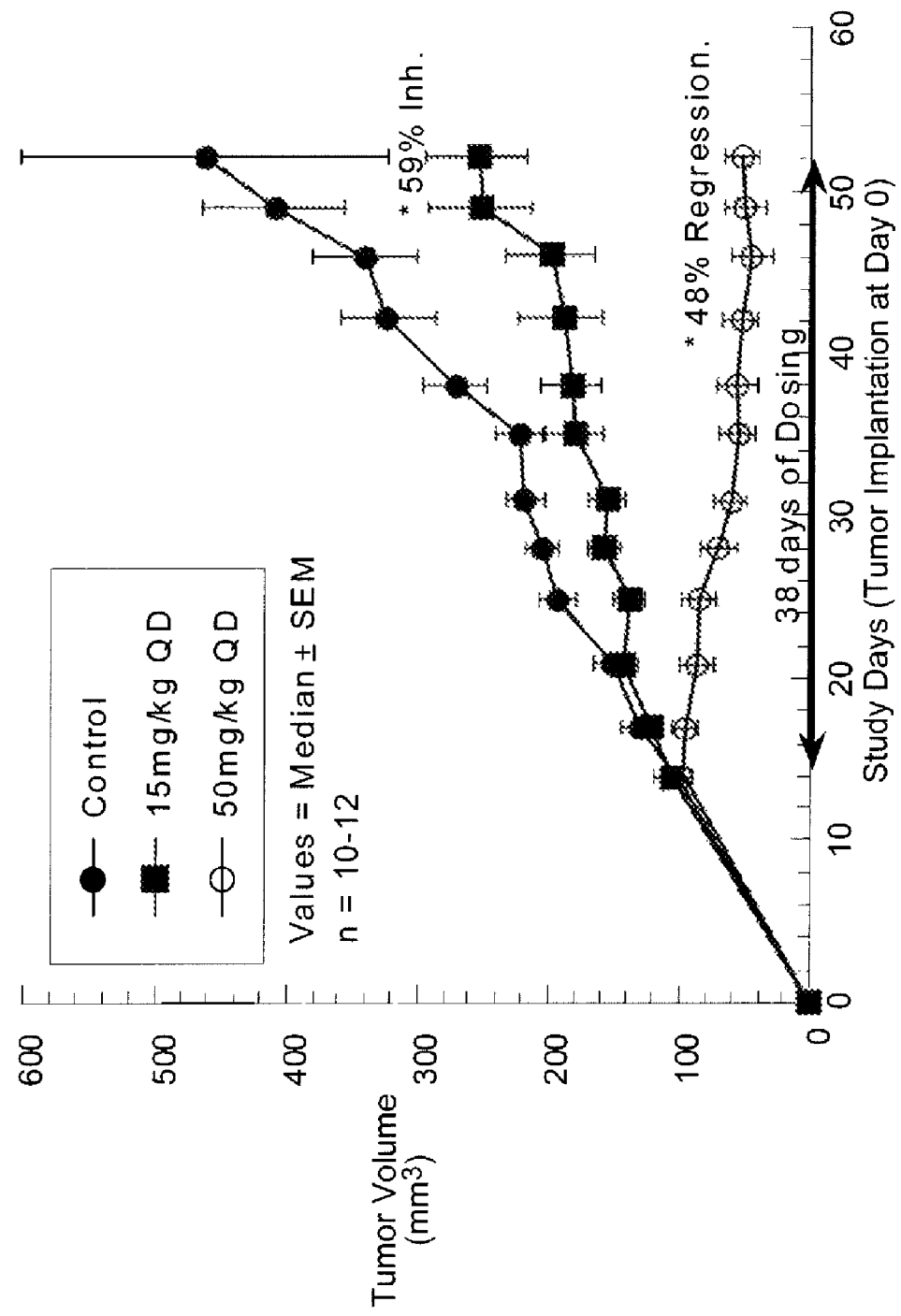

METHOD OF TREATING ABNORMAL CELL GROWTH

This application is a 371 application of PCT/IB2006/003397, filed on Nov. 23, 2006, which claims the benefit of U.S. Provisional Application No. 60/742,766 filed on Dec. 5, 2005, and U.S. Provisional Application No. 60/864,637 filed on Nov. 7, 2006, the contents of which are hereby incorporated by reference in their entireties.

FIELD OF THE INVENTION

The present invention relates to the use of c-Met/HGFR inhibitors for treating abnormal cell growth in mammals. In particular, the invention provides methods of treating mammals suffering from cancer.

BACKGROUND OF THE INVENTION

The compound (R)-3-[1-(2,6-Dichloro-3-fluoro-phenyl)-ethoxy]-5-(1-piperidin-4-yl-1H-pyrazol-4-yl)-pyridin-2-ylamine represented by the formula 1

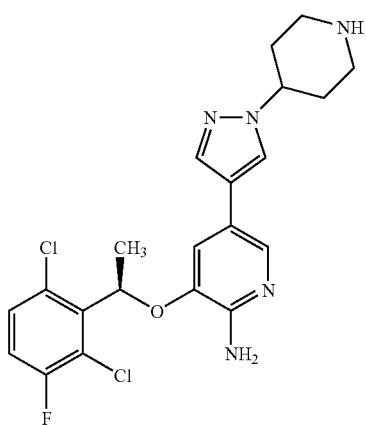

1 is a potent small-molecule inhibitor of c-Met/HGFR (hepatocyte growth factor receptor) kinase and ALK (anaplastic lymphoma kinase) activity. Compound 1 has anti-tumor properties that are pharmacologically mediated through inhibition of c-Met/HGFR which is involved in the regulation of growth and metastatic progression of a wide variety of tumors types, and ALK which implicated in the pathogenesis of ALCL (anaplastic large cell lymphoma). Compound 1 is disclosed in International Patent Application No. PCT/IB2005/002837 and U.S. patent application Ser. No. 11/212,331, both of which are herein incorporated by reference in their entirety. Additionally, the racemate of compound 1 is disclosed in International Patent Application No. PCT/IB05/002695 and U.S. patent application Ser. No. 11/213,039, both of which are herein incorporated by reference in their entirety.

Human cancers comprise a diverse array of diseases that collectively are one of the leading causes of death in developed countries throughout the world (American Cancer Society, Cancer Facts and Figures 2005. Atlanta: American Cancer Society; 2005). The progression of cancers is caused by a complex series of multiple genetic and molecular events including gene mutations, chromosomal translocations, and karyotypic abnormalities (Hanahan D, Weinberg R A. The hallmarks of cancer. Cell 2000; 100: 57-70). Although the underlying genetic causes of cancer are both diverse and complex, each cancer type has been observed to exhibit common traits and acquired capabilities that facilitate its progression. These acquired capabilities include dysregulated cell growth, sustained ability to recruit blood vessels (i.e., angiogenesis), and ability of tumor cells to spread locally as well as metastasize to secondary organ sites (Hanahan D, Weinberg R A. The hallmarks of cancer. Cell 2000; 100: 57-70). Therefore, the ability to identify novel therapeutic agents that 1) inhibit molecular targets that are altered during cancer progression or 2) target multiple processes that are common to cancer progression in a variety of tumors presents a significant unmet need.

An extensive body of literature indicates that c-Met/HGFR is one of the most frequently mutated or otherwise abnormally activated RTKs in various human cancers (Christensen J G, Burrows J, Salgia R. c-Met as a target in human cancer and characterization of inhibitors for therapeutic intervention. Cancer Letters 2005; 225: 1-26). Tumor types in which c-Met/HGFR was reported to be genetically altered by mutation or gene amplification include but are not limited to oncology indications with a strong unmet medical need such as renal, metastatic colorectal, glioma, non-small cell lung, gastric, and head and neck cancers (Christensen J G, Burrows J, Salgia R. c-Met as a target in human cancer and characterization of inhibitors for therapeutic intervention. Cancer Letters 2005; 225: 1-26).

HGFR mutations have been implicated in renal carcinoma (See, for example, L. Schmidt, K. Junker, N. Nakaigawa, T. Kinjerski, G. Weirich, M. Miller, et al., Novel mutations of the MET proto-oncogene in papillary renal carcinomas, Oncogene 1999; 18: 2343-2350; L. Schmidt, F. M. Duh, F. Chen, T. Kishida, G. Glenn, P. Choyke, et al., Germline and somatic mutations in the tyrosine kinase domain of the MET proto-oncogene in papillary renal carcinomas, Nat. Genet. 1997; 16: 68-73; L. Schmidt, K. Junker, G. Weirich, G. Glenn, P. Choyke, I. Lubensky, et al., Two North American families with hereditary papillary renal carcinoma and identical novel mutations in the MET proto-oncogene, Cancer Res. 1998; 58: 1719-1722). HGFR mutations have been tied to head and neck carcinoma (See, for example, M. F. Di Renzo, M. Olivero, T. Martone, A. Maffe, P. Maggiora, A. D. Stefani, et al., Somatic mutations of the MET oncogene are selected during metastatic spread of human HNSC carcinomas, Oncogene 2000; 19: 1547-1555; D. M. Aebersold, O. Landt, S. Berthou, G. Gruber, K. T. Beer, R. H. Greiner, Y. Zimmer, Prevalence and clinical impact of Met Y1253D-activating point mutation in radiotherapytreated squamous cell cancer of the oropharynx, Oncogene 2003; 22: 8519-8523). HGFR mutations have been linked to lung carcinoma (See, for example, P. C. Ma, T. Kijima, G. Maulik, E. A. Fox, M. Sattler, J. D. Griffin, et al., c-MET mutational analysis in small cell lung cancer: novel juxtamembrane domain mutations regulating cytoskeletal functions, Cancer Res. 2003; 63: 6272-6281; P. C. Ma, S. Jagdeesh, R. Jagadeeswaran, E. A. Fox, J. G. Christensen, G. Maulik, et al., c-MET expression/activation, functions, and mutations in non-small cell lung cancer, Proc. Am. Assoc. Cancer Res. 2004; 63: 1875.

Additionally, HGFR mutations have been implicated in other indications including but not limited to childhood hepatocellular carcinomas, human gastric cancer, scirrhous type stomach cancer, colorectal cancer, and malignant melanoma. (See, for example, W. S. Park, S. M. Dong, S. Y. Kim, E. Y. Na, M. S. Shin, J. H. Pi, et al., Somatic mutations in the kinase domain of the Met/hepatocyte growth factor receptor gene in childhood hepatocellular carcinomas, Cancer Res. 1999; 59: 307-310; J. H. Lee, S. U. Han, H. Cho, B. Jennings, B. Gerrard, M. Dean, et al., A novel germ line juxtamembrane Met mutation in human gastric cancer, Oncogene 2000; 19: 4947-4953; A. Lorenzato, M. Olivero, S. Patane, E. Rosso, A. Oliaro, P. M. Comoglio, M. F. Di Renzo, Novel somatic mutations of the MET oncogene in human carcinoma metastases activating cell motility and invasion, Cancer Res. 2002; 62: 7025-7030; H. Kuniyasu, W. Yasui, Y. Kitadai, H. Yokozaki, H. Ito, E. Tahara, Frequent amplification of the c-met gene in scirrhous type stomach cancer, Biochem. Biophys. Res. Commun. 1992; 189: 227-232; M. F. Di Renzo, M. Olivero, A. Giacomini, H. Porte, E. Chastre, L. Mirossay, et al., Overexpression and amplification of the met/HGF receptor gene during the progression of colorectal cancer, Clin. Cancer Res. 1995; 1: 147-154; T. Hara, A. Ooi, M. Kobayashi, M. Mai, K. Yanagihara, I. Nakanishi, Amplification of c-myc, K-sam, and c-met in gastric cancers: detection by fluorescence in situ hybridization, Lab. Invest. 1998; 78: 1143-1153).

The relationship of HGFR mutations to function and oncogenic potential has also been established (See for example, M. Jeffers, L. Schmidt, N. Nakaigawa, C. P. Webb, G. Weirich, T. Kishida, et al., Activating mutations for the met tyrosine kinase receptor in human cancer, Proc. Natl. Acad. Sci. USA 1997; 94: 11445-11450; M. Jeffers, M. Fiscella, C. P. Webb, M. Anver, S. Koochekpour, G. F. Vande Woude, The mutationally activated Met receptor mediates motility and metastasis, Proc. Natl. Acad. Sci. USA 1998; 95: 14417-14422).

Finally, HGFR mutations have been implicated in and studied in mouse tumors (See for example, H. Takayama, W. J. LaRochelle, R. Sharp, T. Otsuka, P. Kriebel, M. Anver, et al., Diverse tumorigenesis associated with aberrant development in mice overexpressing hepatocyte growth factor/scatter factor, Proc. Natl. Acad. Sci. USA 1997; 94: 701-706; T. Otsuka, H. Takayama, R. Sharp, G. Celli, W. J. LaRochelle, D. P. Bottaro, et al., c-Met autocrine activation induces development of malignant melanoma and acquisition of the metastatic phenotype, Cancer Res. 1998; 58: 5157-5167; M. I. Gallego, B. Bierie, L. Hennighausen, Targeted expression of HGF/SF in mouse mammary epithelium leads to metastatic adenosquamous carcinomas through the activation of multiple signal transduction pathways, Oncogene 2003; 22: 8498-8508; C. R. Graveel, Y. Su, L. M. Wang, M. Fiscella, T. Lino, c. Birchmeier, et al., Tumorigenic effects of activating Met mutations in a knock-in mouse model, Proc. Am. Assoc. Cancer Res. 2004; 44: 5102).

NPM-ALK, an oncogenic fusion protein variant of the Anaplastic Lymphoma Kinase, which results from a chromosomal translocation is implicated in the pathogenesis of human anaplastic large cell lymphoma (Pulford K, Morris S W, Turturro F. Anaplastic lymphoma kinase proteins in growth control and cancer. J Cell Physiol 2004; 199: 330-58). The roles of aberrant expression of constitutively active ALK chimeric proteins in the pathogenesis of ALCL have been well defined (Weihua Wan, et. al. Anaplastic lymphoma kinase activity is essential for the proliferation and survival of anaplastic large cell lymphoma cells. Blood First Edition Paper, prepublished online Oct. 27, 2005; DOI 10.1182/blood-2005-08-3254).

The inappropriate activation of c-Met/HGFR (including wild-type c-Met) is also implicated in dysregulation of multiple tumor oncogenic processes such as mitogenesis, survival, angiogenesis, invasive growth, and especially in the metastatic process (Christensen et al, 2005). Furthermore, the expression of c-Met and HGF, its sole, high-affinity ligand, were demonstrated to correlate with poor prognosis or metastatic progression in a number of major human cancers (Christensen et al, 2005). NPM-ALK is implicated in the dysregulation of cell proliferation and apoptosis in ALCL lymphoma cells (Pulford et al, 2004).

SUMMARY OF INVENTION

In one embodiment, the present invention provides a method of treating abnormal cell growth in a mammal in need of such treatment comprising, administering to said mammal a therapeutically effective amount of a compound of the formula 1:

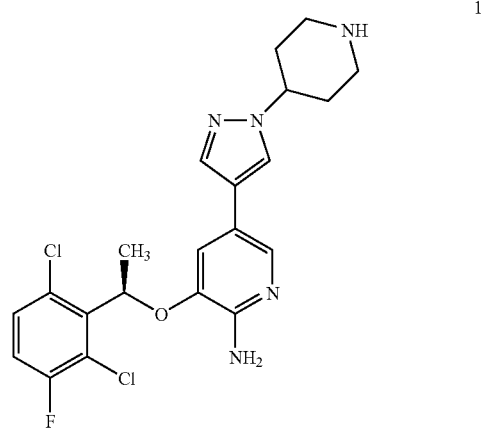

or a pharmaceutically acceptable salt thereof.

In another embodiment, the mammal is a human. In another embodiment, the mammal is a dog.

In another embodiment, the abnormal cell growth is mediated by at least one genetically altered tyrosine kinase. In another embodiment, the abnormal cell growth is mediated by hepatocyte growth factor receptor (c-Met/HGFR) kinase or anaplastic lymphoma kinase (ALK). In another embodiment, the abnormal cell growth is mediated by hepatocyte growth factor receptor (c-Met/HGFR) kinase. In another embodiment, the abnormal cell growth is mediated by anaplastic lymphoma kinase (ALK).

In another embodiment, the abnormal cell growth is cancer. In another embodiment, the cancer is selected from lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, and combinations thereof.

In yet another embodiment, the cancer is selected from the group consisting of non-small cell lung cancer (NSCLC), squamous cell carcinoma, hormone-refractory prostate cancer, papillary renal cell carcinoma, colorectal adenocarcinoma, neuroblastomas, anaplastic large cell lymphoma (ALCL) and gastric cancer.

In yet another embodiment, the compound or pharmaceutically acceptable salt thereof is administered as a pharmaceutical composition comprising the compound of the formula 1 and at least one pharmaceutically acceptable carrier.

In yet another embodiment, the present invention provides a method of inhibiting c-Met/HGFR kinase activity in a cell by administering a compound of the formula 1:

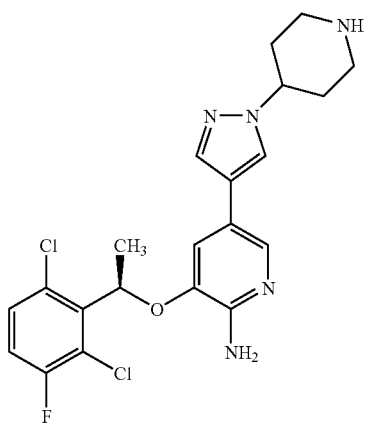

or a pharmaceutically acceptable salt thereof.

In yet another embodiment, the cell is selected from the group consisting of A549 Human Lung Carcinoma, GTL-16 Human Gastric carcinoma, HT29 Human Colon Carcinoma, Colo205 Human Colon Carcinoma, A498 Human Renal Carcinoma, 786-O Human Renal Carcinoma, MBA-MD-231 Human Breast Carcinoma, Madlin-Darby Canine Kidney (MDCK) Epithelial cells, MDCK cells engineered to express P-glycoprotein (MDCK-MDR1), mIMCD3 Mouse Kidney Epithelial, HUVEC (human umbilical vein endothelial cells), Caki-1 Renal Carcinoma, and NIH-3T3 cells engineered to express human wild type c-Met/HGFR and mutated c-Met/HGFRs including HGFR-V1092I, HGFR-H1094R, HGFR-Y1230C, and HGFR-M1250T.

BRIEF DESCRIPTION OF THE DRAWINGS

FIG. 2: Athymic mice bearing established GTL-16 tumors were administered compound 1 orally at the indicated dose or vehicle alone for 11 days.

FIG. 3: Athymic mice bearing established U87MG tumors (150 mm$^3$) were administered compound 1 orally at the indicated dose or vehicle alone for 9 days.

FIG. 4: Daily oral administration of compound 1 to athymic mice bearing large established GTL-16 tumor xenografts.

FIG. 5: Daily oral administration of compound 1 to athymic mice bearing established NCI-H441 or PC-3 tumor xenografts. FIG. 5A: Tumor regression in athymic mice bearing established NCI-H441.

FIG. 6: Antitumor efficacy of compound 1 in an NPM-ALK-dependent lymphoma model (Karpas 299 ALCL Model)

DETAILED DESCRIPTION OF THE INVENTION

Figure 1:
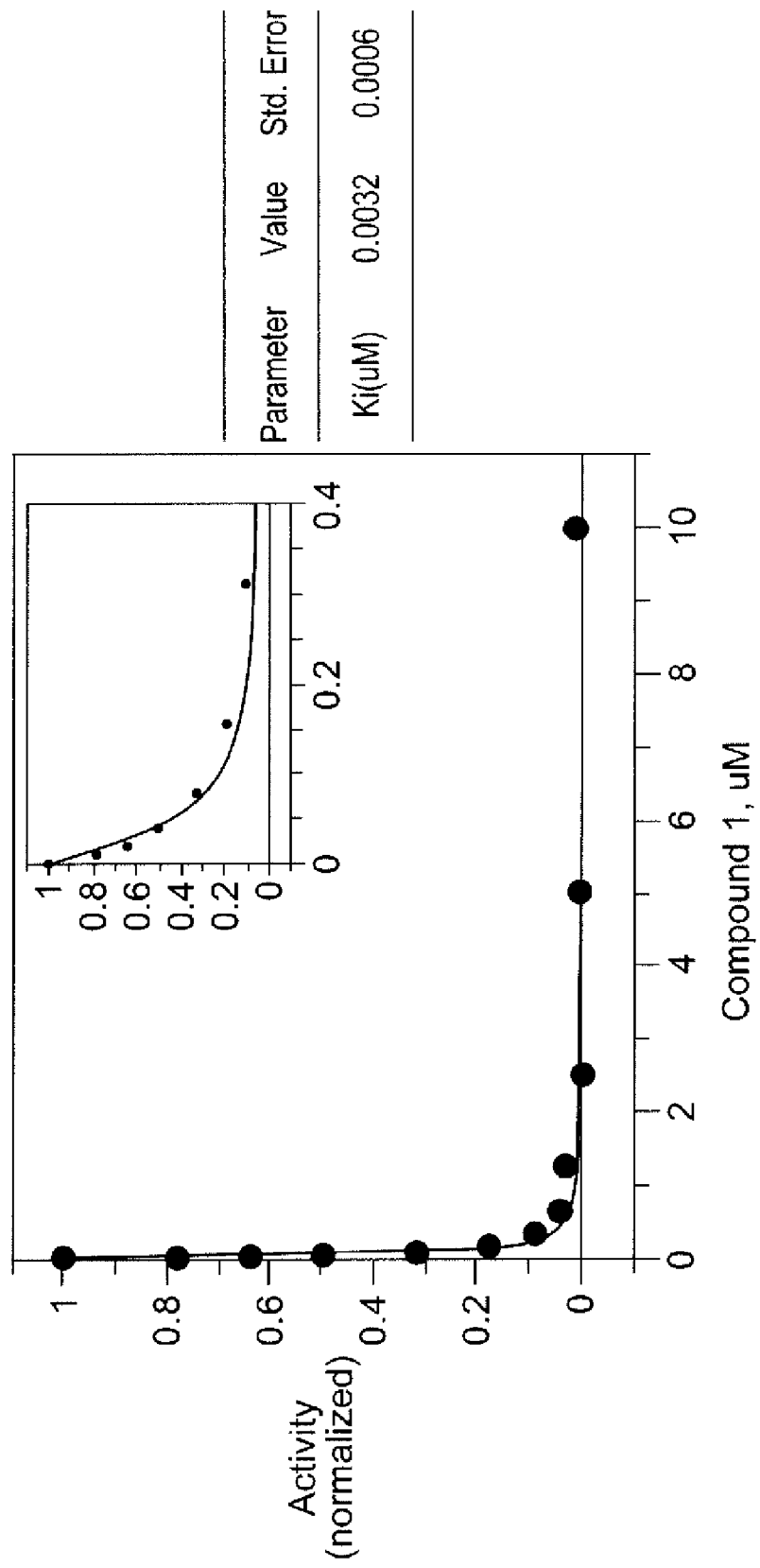
FIG. 1: ATP-competitive inhibition of recombinant, human c-Met/HGFR kinase activity by compound 1.

Unless indicated otherwise, all references herein to the inventive compounds include references to salts, solvates, hydrates and complexes thereof, and to solvates, hydrates and complexes of salts thereof, including polymorphs, stereoisomers, and isotopically labeled versions thereof.

Definitions

As used herein, unless otherwise indicated, the term "abnormal cell growth" refers to cell growth that is independent of normal regulatory mechanisms (e.g., loss of contact inhibition).

As used herein, unless otherwise indicated, the term "treating", means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above.

As used herein the term "pharmaceutically acceptable salts" includes acid addition and base salts (including disalts).

Suitable acid addition salts are formed from acids which form non-toxic salts. Examples include the acetate, aspartate, benzoate, besylate, bicarbonate/carbonate, bisulphate/sulfate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminum, arginine, benzathine, calcium, choline, diethylamine, diolamine, glycine, lysine, magnesium, meglumine, olamine, potassium, sodium, tromethamine and zinc salts.

For a review on suitable pharmaceutically acceptable salts, see "Handbook of Pharmaceutical Salts Properties, Selection, and Use" by Stahl and Wermuth (Wiley-VCH, Weinheim, Germany, 2002), the disclosure of which is incorporated herein by reference in its entirety.

A pharmaceutically acceptable salt of the inventive compounds can be readily prepared by mixing together solutions of the compound and the desired acid or base, as appropriate. The salt may precipitate from solution and be collected by filtration or may be recovered by evaporation of the solvent. The degree of ionization in the salt may vary from completely ionized to almost non-ionized.

The compounds of the invention may exist in both unsolvated and solvated forms. The term 'solvate' is used herein to describe a molecular complex comprising the compound of the invention and one or more pharmaceutically acceptable solvent molecules, for example, ethanol. The term 'hydrate' is employed when the solvent is water. Pharmaceutically acceptable solvates in accordance with the invention include hydrates and solvates wherein the solvent of crystallization may be isotopically substituted, e.g. $D_2O$, $d_6$-acetone, $d_6$-DMSO.

The invention also includes isotopically-labeled compounds, which are identical to compound 1, except that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, sulfur, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Compounds of the present invention and pharmaceutically acceptable salts of said compounds, which contain the aforementioned isotopes and/or other isotopes of other atoms, are within the scope of this invention. Certain isotopically-labeled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. An isotopically labeled compound 1 of this invention can generally be prepared by carrying out the procedures described for the non-labeled compound, substituting a readily available isotopically labeled reagent for a non-isotopically labeled reagent.

Also included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionized, partially ionized, or non-ionized. For a review of such complexes, see J Pharm Sci, 64 (8), 1269-1288 by Haleblian (August 1975), the disclosure of which is incorporated herein by reference in its entirety.

Oral Administration

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, solid solution, liposome, films (including muco-adhesive), ovules, sprays and liquid formulations.

Liquid formulations include suspensions, solutions, syrups and elixirs. Such formulations may be used as fillers in soft or hard capsules and typically include a pharmaceutically acceptable carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986 by Liang and Chen (2001), the disclosure of which is incorporated herein by reference in its entirety.

For tablet dosage forms, depending on dose, the drug may make up from 1 wt % to 80 wt % of the dosage form, more typically from 5 wt % to 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrant will comprise from 1 wt % to 25 wt %, preferably from 5 wt % to 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally include surface active agents, such as sodium lauryl sulfate and polysorbate 80, and glidants such as silicon dioxide and talc. When present, surface active agents are typically in amounts of from 0.2 wt % to 5 wt % of the tablet, and glidants typically from 0.2 wt % to 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally are present in amounts from 0.25 wt % to 10 wt %, preferably from 0.5 wt % to 3 wt % of the tablet.

Other conventional ingredients include anti-oxidants, colorants, flavoring agents, preservatives and taste-masking agents.

Exemplary tablets contain up to about 80 wt % drug, from about 10 wt % to about 90 wt % binder, from about 0 wt % to about 85 wt % diluent, from about 2 wt % to about 10 wt % disintegrant, and from about 0.25 wt % to about 10 wt % lubricant.

Tablet blends may be compressed directly or by roller to form tablets. Tablet blends or portions of blends may alternatively be wet-, dry-, or melt-granulated, melt congealed, or extruded before tableting. The final formulation may include one or more layers and may be coated or uncoated; or encapsulated.

The formulation of tablets is discussed in detail in "Pharmaceutical Dosage Forms: Tablets, Vol. 1", by H. Lieberman and L. Lachman, Marcel Dekker, N.Y., N.Y., 1980 (ISBN 0-8247-6918-X), the disclosure of which is incorporated herein by reference in its entirety.

Solid formulations for oral administration may be formulated to be immediate and/or modified release. Modified release formulations include delayed-, sustained-, pulsed-, controlled-, targeted and programmed release.

Suitable modified release formulations are described in U.S. Pat. No. 6,106,864. Details of other suitable release technologies such as high energy dispersions and osmotic and coated particles can be found in Verma et al, Pharmaceutical Technology On-line, 25(2), 1-14 (2001). The use of chewing gum to achieve controlled release is described in WO 00/35298. The disclosures of these references are incorporated herein by reference in their entireties.

Parenteral Administration

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including micro needle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilization, may readily be accomplished using standard pharmaceutical techniques well known to those skilled in the art.

The solubility of compounds of the invention used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and PGLA microspheres.

Topical Administration

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated; see, for example, J Pharm Sci, 88 (10), 955-958 by Finnin and Morgan (October 1999). Other means of topical administration include delivery by electroporation, iontophoresis, phonophoresis, sonophoresis and micro needle or needle-free (e.g. Powderject™, Bioject™, etc.) injection. The disclosures of these references are incorporated herein by reference in their entireties.

Formulations for topical administration may be formulated to be immediate and/or modified release. Modified release formulations include delayed-, sustained-, pulsed-, controlled-, targeted and programmed release.

Inhaled/Intranasal Administration

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may include a bioadhesive agent, for example, chitosan or cyclodextrin.

The pressurized container, pump, spray, atomizer, or nebulizer contains a solution or suspension of the compound(s) of the invention comprising, for example, ethanol, aqueous ethanol, or a suitable alternative agent for dispersing, solubilizing, or extending release of the active, a propellant(s) as solvent and an optional surfactant, such as sorbitan trioleate, oleic acid, or an oligolactic acid.

Prior to use in a dry powder or suspension formulation, the drug product is micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying.

Capsules (made, for example, from gelatin or HPMC), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomizer using electrohydrodynamics to produce a fine mist may contain from 1 µg to 20 mg of the compound of the invention per actuation and the actuation volume may vary from 1 µL to 100 µL. A typical formulation includes a compound of the invention, propylene glycol, sterile water, ethanol and sodium chloride. Alternative solvents which may be used instead of propylene glycol include glycerol and polyethylene glycol.

Suitable flavors, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, poly(DL-lactic-coglycolic acid (PGLA). Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing a desired mount of the compound of the invention. The overall daily dose may be administered in a single dose or, more usually, as divided doses throughout the day.

Rectal/Intravaginal Administration

Compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

Ocular Administration

Compounds of the invention may also be administered directly to the eye or ear, typically in the form of drops of a micronized suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

Other Technologies

Compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubilizer. Most commonly used for these purposes are alpha-, beta- and gamma-cyclodextrins, examples of which may be found in PCT Publication Nos. WO 91/11172, WO 94/02518 and WO 98/55148, the disclosures of which are incorporated herein by reference in their entireties.

Dosage

The amount of the active compound administered will be dependent on the subject being treated, the severity of the disorder or condition, the rate of administration, the disposition of the compound and the discretion of the prescribing physician. However, an effective dosage is typically in the range of about 0.001 to about 100 mg per kg body weight per day, preferably about 0.01 to about 35 mg/kg/day, in single or divided doses. For a 70 kg human, this would amount to about 0.07 to about 7000 mg/day, preferably about 0.7 to about 2500 mg/day. In some instances, dosage levels below the lower limit of the aforesaid range may be more than adequate, while in other cases still larger doses may be used without causing any harmful side effect, with such larger doses typically divided into several smaller doses for administration throughout the day.

Kit-of-Parts

Inasmuch as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions. Thus the kit of the invention includes two or more separate pharmaceutical compositions, at least one of which contains a compound of the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically includes directions for administration and may be provided with a memory aid.

EXAMPLES

In-Vitro Assays

Materials and Methods
In-Vitro Methods
Biochemical Kinase Assay Methods

The biochemical $K_i$ values of compound 1 for the inhibition of the c-Met/HGFR kinase were determined utilizing a general procedure to monitor NADH oxidation that is coupled to ATP turnover as follows. Compounds and kinase assay reagents are introduced into test wells and incubated for 10 minutes at 37° C. The assay is initiated by addition of the c-Met/HGFR enzyme. Enzyme inhibitors reduce the measured activity of the enzyme. In the continuous-coupled spectrophotometric assay the time-dependent production of ADP by the kinase is determined by analysis of the rate of consumption of NADH by measurement of the decrease in absorbance at 340 nm. As the kinase enzyme produces ADP it is re-converted to ATP by reaction with phosphoenol pyruvate and pyruvate kinase. Pyruvate is also produced in this reaction. Pyruvate is subsequently converted to lactate by reaction with lactate dehydrogenase, which simultaneously converts NADH to NAD. NADH has a measurable absorbance at 340 nm whereas NAD does not. Therefore, the assay endpoint is measured by spectrophotometry at 340 nm at the designated time points.

Cell Signaling Biochemical Kinase Assay Methods (Upstate)

Kinases were pre-diluted to a 10× working concentration prior to addition into the assay. Briefly, substrates were dissolved and diluted to working stocks in deionizer water, apart from histone H1 (10× working stock in 20 mM MOPS pH 7.4), PDKtide (10× working stock in 50 mM Tris pH 7.0) and ATF2 (which is typically stored at a 20× working stock in 50 mM Tris pH 7.5, 150 mM NaCl, 0.1 mM EGTA, 0.03% Brij-35, 50% glycerol, 1 mM benzamidine, 0.2 mM PMSF and 0.1% □-mercaptoethanol). The biochemical enzyme of interest was then assayed in a final reaction volume of 25 µl containing 5-10 mU of the enzyme of choice incubated with 8 mM MOPS pH 7.0, 0.2 mM EDTA, 50 µM EAIYAAP-FAKKK, 10 mM MgAcetate and $^{32}$P-ATP (specific activity approx. 500 cpm/µmol, concentration as required). The reaction is initiated by the addition of the MgATP mix. After incubation for 40 minutes at room temperature, the reaction is stopped by the addition of 5 µl of a 3% phosphoric acid solution. 10 µl of the reaction is then spotted onto a P30 filtermat and washed three times for 5 minutes in 75 mM phosphoric acid and once in methanol prior to drying and scintillation counting.

Cell Lines

Cell lines utilized to evaluate compound 1 in in-vitro studies were as follows: A549 Human Lung Carcinoma, GTL-16 Human Gastric carcinoma, HT29 Human Colon Carcinoma, Colo205 Human Colon Carcinoma, A498 Human Renal Carcinoma, 786-O Human Renal Carcinoma, MBA-MD-231 Human Breast Carcinoma, Madlin-Darby Canine Kidney (MDCK) Epithelial cells, MDCK cells engineered to express P-glycoprotein (MDCK-MDR1), mlMCD3 Mouse Kidney Epithelial, HUVEC (human umbilical vein endothelial cells); NIH-3T3 cells engineered to express human wild type c-Met/HGFR and mutated c-Met/HGFRs including HGFR-V1092I, HGFR-H1094R, HGFR-Y1230C, and HGFR-M1250T. Cell lines utilized to evaluate inhibition of phosphorylation of other tyrosine kinases were as follows: KARPAS 299, SU-DHL-1, and Jurkat human lymphoma cells, human umbilical vein endothelial cells (HUVEC), Human macro vascular endothelial cells (HMVEC), Porcine Aorta Endothelial (PAE) cells engineered to express human VEGFR2, PDGFRβ, TrkA and TrkB; NIH-3T3 cells engineered to express human Ron, Axl, Sky and EGFR/Tie-2 chimera; HEK293 cells engineered to express human IRK, Chinese Hamster Ovary (CHO-B) cells engineered to express human Ron, BaF3 cells engineered to express human BCR-Abl. All the engineered cell lines were generated at Pfizer, GTL-16 gastric carcinoma cells were a gift from Dr. Paolo Comoglio (University Torino Medical School, Candiolo, Italy), HUVEC and HMVEC (Human Macrovascular Endothelial Cell) were purchased from Clonetics, Inc. (Walkersville, Md.), and the others were from ATCC (Manassas, Va.). Unless otherwise indicated, cell culture reagents were obtained from Life Technologies, Inc. (Gaithersburg, Md.). Cells were maintained at 37° C. in a humidified atmosphere with 5-10% $CO_2$ and maintained using standard cell culture techniques.

Antibodies and Growth Factors

Antibodies were utilized to evaluate compound 1 in in vitro ELISA and immunoblotting studies were as follows: anti-total human c-Met/HGFR and anti-phospho Zap70 were from Zymed/Invitrogen, Carlsbad, Calif.; anti-total Ron, anti-total FGFR1, anti-total PDGFRβ, anti-total Trk, anti-total Tie-2, and anti-phospho tyrosine (PY-20) were from Santa Cruz Biotechnology, Santa Cruz, Calif.; anti-total Axl and anti-total mouse c-Met/HGFR were form R&D Systems, Minneapolis, Minn.; anti-total IRK from BD Pharmingen, San Diego, Calif.; anti-VEGFR2 from Novus Biologicals, Littleton, Colo.; anti-phospho-c-Met/HGFR, anti-total and -phospho ALK, anti-total c-ABL, anti-total and phosphor Gab1, anti-total and phospho AKT, anti-total and phosphor-MAPK44/42, anti-phospho Raf, Mek1/2, P90RSK, and STAT5 were from Cell Signaling Technologies, Boston, Mass.

Most Growth factors utilized in cell assays were from R&D Systems, Minneapolis, Minn., except BDGF from Gibco-BRL/Invitrogen, Carlsbad, Calif., and EGF from Roche Applied Science, Indianapolis, Ind.

Cellular Kinase Phosphorylation Assays

Cellular assays (i.e., ELISA or immunoblot) used to directly determine the ability of compound 1 to inhibit ligand-dependent or constitutive kinase phosphorylation were performed using a variety of serum-starved cells.

Cell Preparation

Cells were seeded in 96 well plates in growth media (media supplemented with 10% fetal bovine serum-FBS) and cultured overnight at 37° C. to facilitate attachment to assay plates. After attachment, growth media was removed and cells were cultured in serum-free media (with 0.04% BSA). Serial dilutions of compound 1 were performed, appropriate controls or designated concentrations of compound 1 were added to each well, and cells were incubated at 37° C. for 1 hour. In experiments investigating ligand-dependent RTK phosphorylation, corresponding growth factors (e.g., HGF, MSP, Gas6, EGF, NGF, BDNF, insulin, VEGF, or PDGF BB) were added to cells for 8 to 20 minutes. $H_2O_2$ was used to stimulate human Axl phosphorylation in HUVEC cells as described (Konishi, A., Aizawa, T. Mohan, A., Korshunov, V. A. and Berk, B. C., Hydrogen peroxide activates the Gas6-Axl pathway in vascular smooth muscle cells. *The Journal of Biological Chemistry*, 279:28766-28770 (2004)). Constitutive kinase phosphorylation was measured in absence of addition of exogenous ligand for cell lines with constitutively active kinase activity (e.g., c-Met/HGFR in GTL-16 cells, NPM-ALK in Karpas 299 cells, Ron in Ron-CHO-B cells, and BCR-Abl in BCR-Abl BaF3 cells). After incubation of cells with compound 1 and/or appropriate ligands for the designated times, cells were washed once with 1 mM $Na_3VO_4$ in HBSS and then lysed using Lysis Buffer (Cell Signaling Technologies, Boston Mass.).

ELISA Assay

Phosphorylation of protein kinases of interest was assessed by a sandwich ELISA method utilizing capture antibodies specific for each protein and a detection antibody specific for phosphorylated tyrosine residues. In each ELISA assay, protein lysates generated from various cell lines treated with appropriate RTK ligands and/or compound 1 were transferred to a 96 well plate that was pre-coated with the corresponding antibodies including anti-c-Met/HGFR, -Ron, -Axl, -Sky, -IR, -Tie2, -KDR, -PDGFR β, -Zap70, and etc. Antibody-coated plates were incubated in presence of protein lysates at 4° C. overnight and washed with 1% Tween 20 in PBS seven times. HRP-PY20 (horseradish peroxidase-conjugated anti-total-phosphotyrosine, Santa Cruz Biotechnology, Santa Cruz, Calif.) was diluted 1:500 in blocking buffer (Pierce, Rockford, Ill.) and added to each plate for 30 minutes. Plates were then washed again and TMB peroxidase substrate (Bio-Rad laboratories, Hercules Calif.) was added to initiate the HRP-dependent colorimetric reaction. The reaction was stopped by adding $0.09NH_2SO_4$. Plates were measured at OD-450 nm using a spectrophotometer. $IC_{50}$ values were calculated by concentration-response curve fitting utilizing a four-parameter analytical method in an Excel-based template.

Immunoblotting

The ability of compound 1 to inhibit cellular kinase phosphorylation was also measured by immunoblotting method. Cells were treated with dilutions of compound 1 in serum-free media and lysed for protein extraction as described above. Cell lysates were normalized for protein concentration by BSA assay (Pierce, Rockford, Ill.) and specific antibodies were used immunoprecipitate proteins of interest. Immuno-precipitated proteins were separated by SDS-PAGE and immunoblotting with anti-phosphotyrosine antibodies was performed to determine relative levels of phosphorylated proteins at each drug concentration. This immunoblotting method was also used to determine total protein levels for the molecules of interest.

Cell Proliferation and Survival Assays

Cell Proliferation Assay

Tumor cells were seeded in 96 well plates at low density in growth media (media supplemented with 10% fetal bovine serum-FBS) and cultured overnight at 37° C. The following day, growth media was removed and cells were cultured in serum-free media (0% FBS and 0.04% BSA). Serial dilutions of compound 1 were performed, appropriate controls or designated concentrations of compound 1 were added to each well, and cells were incubated at 37° C. for 24 to 72 hours. A MTT assay (Promega, Madison, Wis.) was then performed to determine the relative cell numbers. $IC_{50}$ values were calculated by concentration-response curve fitting utilizing a four-parameter analytical method.

Apoptosis/Cell Survival Assay

GTL-16 cells were seeded in 96 well plates at 40,000 cells/well. Designated concentrations of PF-02341066 or vehicle were added to the wells in serum free media. Cells were incubated in 37° C., 5% $CO_2$ for 48 hours. The ssDNA Apoptosis ELISA kit (Chemicon International) was used to detect Apoptosis.

HGF-Stimulated HUVEC Survival Assay

HUVEC cells (passage 3) were grown to confluence in EGM2 media (Walkersville, Md.). Cells were seeded in 96 well plates in EGM2 media at high density (20,000 to 30,000/well) and incubated for 5 to 6 hours to allow for cell attachment. After attachment, cells were cultured in serum-free media (Cell Applications, San Diego, Calif.) overnight at 37° C. at 5% $CO_2$. The following day, cells were exposed to the Starvation Media (Cell Applications, San Diego, Calif.) for 5 hours. Compound 1 was serially diluted in serum-free media and appropriate controls or designated concentrations of compound 1 were added to each well. After 1 hour, human recombinant HGF (R&D Systems, Minneapolis, Minn.) was added to designated wells to achieve a final concentration of 100 ng/mL. A MTT assay (Promega) was then performed after 48 to 72 hours to determine the relative cell numbers. $IC_{50}$ values were calculated by concentration-response curve fitting utilizing a four-parameter analytical method.

HGF-Dependent Cell Migration and Invasion Assays

NCI-H441 Cell Migration and Matrigel Invasion Assays

The effect of compound 1 on HGF-stimulated NCI-H441 human non-small cell lung carcinoma cell migration and matrigel invasion was determined utilizing a commercially available cell migration and invasion system (BD Biosciences, San Jose, Calif.). Cells in log growth phase were trypsinized and suspended in serum-free media (with 0.04% BSA) at a density of 400,000 cells/mL. Compound 1 was serially diluted in serum-free media, designated concentrations were added to suspended cells, and cells were incubated at room temperature for 30 minutes. Designated control or treated suspended cells (0.5 mL) were added to each migration or invasion chamber (i.e., plate inserts). In addition, 25 ng/mL HGF (0.75 mL) was added to the lower well of each companion plate as a chemotractant to attract cells from migration or invasion chamber plate inserts inserted at the top of the companion plate and cells were incubated at 37° C. for 22 hours. Cells that invaded or migrated to the lower well of the plate were then fixed and nuclei were stained (1 ug/mL DAP1 in 100% MeOH) for 15 minutes at 37° C. Cells were subsequently washed twice using TBS solution. Five microscopic images were taken from each well and the cell number for migration or invasion was determined under each condition using Image-Pro Plus software (Media Cybernetics, Silver Spring, Md.). $IC_{50}$ values were calculated by concentration-response curve fitting utilizing a four-parameter analytical method.

HUVEC Matrigel Invasion Assay

An ACEA RT-CES System (ACEA biologicals, San Diego, Calif.) was used to determine the effect of compound 1 on HUVEC matrigel invasion in vitro. ACEA electrosensing 96-well plates were coated with 50 μl of 0.001% fibronectin and 100 ng/mL HGF in PBS and incubated at 37° C. for 1 hour and at 4° C. for 30 minutes. After washing each plate with PBS at 4° C., Matrigel (BD Biosciences, San Jose, Calif.) was diluted 1:40 in Starvation Media (SM, Cell Applications, San Diego, Calif.), supplemented with HGF (100 ng/mL) and/or different concentrations of compound 1, added (50 μL) to designated wells, and allowed to solidify at 37° C. for 2 hours. HUVEC cells were cultured in serum-free media (Cell Applications, San Diego, Calif.) for 5 hours and then in SM for 2 hours. Cells were subsequently collected in SM at 60,000 cells/mL and treated with 100 ng/mL HGF and/or appropriate of compound 1 for 30 minutes at 37° C. The HUVEC cell suspension (100 μL) under designated conditions was transferred to the top of the Matrigel layer in designated wells of the coated ACEA plate. The ACEA plate was then connected to the ACEA Device Station at 37° C., 95% air:5% $CO_2$ and monitored in real time by an ACEA Sensor Analyzer for 48 hours. Electronic sensors embedded on the bottom of the ACEA plates detected HUVEC cells that invaded through Matrigel. The relative number (cell index) of invaded HUVEC cells was determined utilizing ACEA RT-CES™ Integrated Software. $IC_{50}$ values were calculated by concentration-response curve fitting utilizing a four-parameter analytical method.

MDCK Cell Scattering Assay

MDCK cells were seeded at low density (25 cells/well) in a 96-well plate in media supplemented with 10% FBS and grown until small colonies of 10-15 cells appeared. Cells were then stimulated with HGF (50 ng/mL) in the presence of various concentrations of compound 1 diluted in growth medium. After overnight incubation, colonies were fixed and stained with 0.2% crystal violet in 10% buffered formalin and assessed for scattering at each concentration visually.

HMVEC Vascular Sprouting Assay

Five hundred HMVEC were added to EGM-2 medium containing 0.24% methylcellulose and transferred to U-bottom 96-well plates to form spheroids overnight. Spheroids were collected and mixed into 2 mg/mL fibrinogen solution containing 4-8% FBS±compound in 48-well plates coated with thrombin (2 mL of 5,000 U/mL). The resulting 3-D fibrin gel was covered with EGM-2 containing 4-8% FBS and incubated at 37° C., 95% air/5% $CO_2$. Endothelial tube formation was observed daily under an inverted microscope. Images were captured on day 7 by a digital camera (Olympus BX60) connected to the microscope. Compound 1 was added at several concentrations and vascular sprouting was visually assessed.

Cell Cycle and Apoptosis Analysis by Flow Cytometry

The effect of compound 1 on NPM-ALK-dependent cell cycle distribution and apoptosis of human lymphoma cells was evaluated by flow cytometric analysis (FACSCalibur, BD Biosciences, San Jose, Calif.). Karpas 299 and SU-DHL-1 human lymphoma cells were treated with compound 1 for 24 to 48 hours in growth media (RPMI+10% FBS). Cells were washed with PBS twice, fix and permeabilized with BDCytofix/Cytoperm Solution for 20 minutes at 4° C. Cell cycle distribution and apoptosis of lymphoma cells was assessed utilizing the CycloTest Plus DNA Reagent Kit (BD Biosciences). Using this kit cells were washed two times with 1×BD Perm/Wash Buffer, non-ionic detergent and Trypsin were added to isolate nuclei, propidium iodide was added to visualize DNA content, and cells were analyzed by flow cytometry. DNA content (ploidy analysis to determine percent cell number in each cell cycle) was assessed using Cell Quest Pro and analyzed with ModFit LT software (BD Biosciences). The apoptotic peak ($A_0$) was defined as the peak that occurs in channel numbers lower than $G_0/G_1$ peak as described (Darzynkiewicz, Z., Bruno, S., Del-Bino, G., Gorczyca, W., Hotz, M. S., Lassota, P., and Traganos, F., *Cytometry* 13:795-808 (1992)). Apoptosis was also determined by flow cytometric analysis using Annexin V-FITC staining (BD Biosciences, San Jose, Calif.) and also analyzed using FACSCalibur.

In-Vivo Methods

Cell Lines

Unless otherwise indicated, cell culture reagents were obtained from Life Technologies, Inc. (Gaithersburg, Md.). Cells were maintained at 37° C. in a humidified atmosphere with 5-10% $CO_2$ and passaged using standard cell culture techniques. U87MG (human glioblastoma), NCI-H441 (human nom-small cell lung adenocarcinoma), PC-3 (human prostate adenocarcinoma) cells were obtained from and cultured as recommended by the American Type Culture Collection (Bethesda, Md.).

Subcutaneous Xenograft Models in Athymic Mice

Female or male nu/nu or SCID/Beige mice (5-8 weeks old) were obtained from Harlan (Madison, Wis.) or Charles River (Wilmington, Mass.). Animals were maintained under clean room conditions in sterile filter top cages with Alpha-Dri/bed-o-cob comb bedding housed on HEPA-filtered ventilated racks. Animals received sterile rodent chow and water ad libitum. Cells for implantation into athymic mice were harvested and pelleted by centrifugation at 450×g for 5-10 minutes. The cell pellets were washed once and re-suspended in sterile phosphate buffered saline or serum-free medium. Tumor cells were supplemented with 30-50% Matrigel (BD Biosciences, San Jose Calif.) to facilitate tumor take and growth of selected tumor cells as xenografts. Cells (2-5×10$^6$ in 100 µL) were implanted SC into the hindflank region of the mouse and allowed to grow to the designated size prior to the administration of compound for each experiment. Tumor size was determined by measurement with electronic calipers and tumor volume was calculated as the product of its length× width$^2$×0.4.

Ex Vivo Target Modulation (PK/PD) Studies

Tumor and Plasma Processing for In Vivo Pharmacodynamic Studies

Tumor cells expressing constitutively phosphorylated c-Met/HGFR or ALK were implanted subcutaneously in nude mice and allowed to grow untreated to a size of 300-800 mm$^3$. Mice were administered compound 1 as a single oral dose (for acute PK/PD studies) or multiple oral doses (for steady state PK/PD studies) at the designated dose levels. At the indicated times following compound 1 administration, individual mice were humanely euthanized, a blood sample was isolated from the cardiac left ventricle using a syringe primed with heparin sulfate, and tumors were resected. Plasma samples were analyzed for compound 1 concentration using LCMS analysis. Resected tumors were snap frozen on dry ice, pulverized using a liquid nitrogen-cooled cryomortar and pestle, and lysed in cold 1× Cell Lysis Buffer (Cell Signaling Technologies, Boston Mont.)). Proteins were extracted from tumor lysate and protein concentrations were determined using a BSA assay (Pierce, Rockford, Ill.). The level of total or/and phosphorylated proteins of interest in each tumor sample was determined using a capture ELISA method below.

ELISA Assays for Assessment of Pharmacodynamic Inhibition of Kinase Targets

In each ELISA assay, protein lysates that were generated from vehicle- or compound 1-treated tumors were transferred to a 96 well plate that was pre-coated with either anti-c-Met/HGFR (Zymed Lab/Invitrogen, Carlsbad, Calif.) or anti-ALK capture antibodies (Cell Signaling Technologies, Boston Mont.). Antibody-coated plates were incubated in presence of tumor lysates at 4° C. overnight and washed with 1% Tween 20 in PBS seven times. HRP-PY20 (horseradish peroxidase-conjugated anti-total-phosphotyrosine, Santa Cruz Biotechnology, Santa Cruz, Calif.) was diluted 1:500 in blocking buffer (Pierce, Rockford, Ill.) and added to each plate for 30 minutes. Plates were washed again and TMB peroxidase substrate (Bio-Rad laboratories, Hercules Calif.) was added to initiate the HRP-dependent colorimetric reaction. Reactions were stopped by adding 0.09NH$_2$SO$_4$. The optical density (OD) of each vehicle or treatment well was measured at 450 nm using a spectrophotometer. Total phosphorylation of c-Met/HGFR or ALK in tumors resected from compound 1-treated animals was compared with that in tumors resected from vehicle-treated animals at the same time point based on the OD readings. In this evaluation, the inhibition of kinase target phosphorylation by compound 1 in tumors was calculated using the following equation: % Inhibition=100−[(Mean OD treated/Mean OD untreated)×100].

Immunoblotting

Immunoblotting method was also used to determine relative kinase phosphorylation status and total protein levels in tumor samples for the protein of interest. Tumor bearing mice were treated with different doses of compound 1, tumor lysates and protein samples were prepared as described above. Specific antibodies were used immunoprecipitate proteins of interest. Immunoprecipitated proteins were separated by SDS-PAGE and immunoblotting with anti-phosphotyrosine or total antibodies.

Antibodies utilized in immunoblotting studies were as follows: anti-total human c-Met/HGFR from Zymed/Invitrogen, Carlsbad, Calif.; anti-phospho-c-Met/HGFR, anti-total and -phospho ALK, anti-total and phosphor Gab1, anti-total and phospho AKT, anti-total and phosphor-MAPK44/42, STAT5 were from Cell Signaling Technologies, Boston, Mass.

Osmotic Mini-Pump Implantation for In Vivo Infusion Studies

Alzet 1003D and 1007D Osmotic mini-pumps were purchased from Durect Corporation (Cupertino, Calif.). Mini pumps were loaded with solutions of designated concentrations of compound 1, and primed in sterile saline solution at 37° C. until they reached equilibrium at 4 to 5 hours. Pumps were surgically implanted subcutaneously per manufacturer's instructions into left dorsal thoracic area of mice bearing tumors in their right flank region. The incision was closed using surgical clips which were removed after 5-7 days when the skin incision was completely healed. Pump replacement surgery was conducted at the designated time for studies that required infusion time and drug volume that exceeded pump capacity.

Tumor Histology and Immunohistochemistry (IHC)

Tumor specimens to be evaluated for immunohistochemical endpoints were harvested and fixed in 10% buffered formalin with protease and phosphotase inhibitors for 24 hours before being transferred to 70% ethanol. Tumor specimens were subsequently paraffin-embedded and 4 µM sections were cut and baked on to microscope slides. Deparaffinization and antigen retrieval (EDTA-based) was performed following manufacturer instructions using a commercially available decloaking chamber (Biocare Medical, Cat # DC2001). Tumor OCT frozen samples were also collected and sectioned for CD-31 staining. For immunostaining, slides were incubated with the primary antibodies then secondary antibodies, and visualized using either a calorimetric method (DAO Envision-HARP, DAB kit, DAO, Carpentaria, Calif.), or a fluoremetric method (Alexa 488 or Alexa 635, Molecular Probes/Invitrogen, Carlsbad Calif.). All of the immunostained sections were counterstained using hematoxylin. Automated Ventana Discovery XT Staining Module (Ventana Medical Systems, Tucson, Ariz.) was also used to conduct histological staining following manufacturer instructions. Stained sections were analyzed using an Olympus microscope and quantitative analysis of section staining was performed utilizing the ACIS system (Automated Cellular Imaging, Clarient, Irvine Calif.). The slides were also analyzed by in house pathologists using standard clinical methods.

Antibodies utilized in immunohistochemistry studies included anti-phospho-c-Met/HGFR from Biosource Internationals/Invitrogen, Carlbad, Calif.; anti-Ki67 from Dacocytomation, Carpenteria, Calif.; anti-CD31 from Santa Cruz Biotechnology, Santa Cruz, Calif.

Data and Results

Enzymatic Potency of Compound 1 Against the c-Met/HGFR RTK

Compound 1 was demonstrated to be a potent ATP-competitive inhibitor of recombinant, human c-Met/HGFR kinase activity with a mean $K_i$ of 4 nM.

Compound 1 inhibited kinase activity of c-Met/HGFR in a biochemical enzyme assay with a Ki of 3 nM. To investigate kinase selectivity relative to c-Met/HGFR, compound 1 was further evaluated in biochemical kinase screening assays against a panel of >120 recombinant kinases. In these preliminary biochemical kinase selectivity screens, a subset of kinases were identified against which compound 1 exhibited activity such that selectivity for c-Met/HGFR was estimated to be less than 100-fold compared with c-Met/HGFR. The activity of compound 1 against these potential kinase hits was further evaluated in follow-up studies in definitive cell-based kinase selectivity assays (Table 1). The biochemical Ki values of compound 1 for the inhibition of the c-Met/HGFR kinase were determined by monitoring NADH oxidation which is coupled to ATP turnover. Compounds and kinase assay reagents were introduced into test wells and incubated for 10 minutes at 37° C. and the reaction was initiated by adding the c-Met/HGFR. NADH was measured by spectrophotometry at 340 nm at the designated time points.

Kinase Selectivity of Compound 1 in Cell-Based Assays

The selectivity of compound 1 was evaluated in a panel of cell based kinase activity assays for the selected kinases that were potential hits in biochemical assays and other related RTKs (e.g., RON, SKY, IR). In cell-based studies, compound 1 was greater than 1000-fold selective for VEGFR2 and PDGFRβ split-RTKs, greater than 200-fold selective for IR and Lck, and approximately 40-60-fold selective for Axl, Tie2, TrkA, and TrkB, all compared with c-Met/HGFR (A549 $IC_{50}$=8.6 nM). To investigate whether a 50-fold window was sufficient for c-Met/HGFR selectivity in vivo, compound 1 was evaluated for its ability to inhibit Tie-2 phosphorylation in C6 xenografts in nude mice. In this study, no significant inhibition of Tie-2 phosphorylation was observed at any time point following a single PO dose of 50 mg/kg (representing $IC_{99}$ for c-Met/HGFR inhibition over 24 hrs) or 100 mg/kg. This indicates that inhibition of Tie-2, Axl, or TrkA & B would be unlikely at doses up to 2-fold higher than dose levels associated with full inhibition of c-Met/HGFR over 24 h. Compound 1 was 20-30-fold selective for RON kinase which represents a potentially beneficial oncology target due to 1) overexpression and mutation in selected cancers and 2) lack of adverse phenotype in RON-null mice. In contrast to the aforementioned RTKs, compound 1 demonstrated a near equivalent $IC_{50}$ value (24 nM) against an oncogenic form of the ALK RTK (Anaplastic Lymphoma Kinase) fusion protein, NPM-ALK an oncogenic fusion protein variant of the ALK RTK (Anaplastic Lymphoma Kinase), that results from a chromosomal translocation which is implicated in the pathogenesis of human anaplastic large cell lymphoma (ALCL, in a human lymphoma cell line.

Pharmacodynamic Inhibition of c-Met/HGFR RTK Activity in Cells

To confirm that the potent enzymatic activity translated into inhibition of c-Met/HGFR in cells, the ability of compound 1 to inhibit cMet/HGFR phosphorylation in a panel of tumor and endothelial cell lines was evaluated. Compound 1 inhibited HGF-stimulated or constitutive total tyrosine autophosphorylation of wild type c-Met/HGFR with a mean $IC_{50}$ value of 11 nM across a panel of human tumor and endothelial cell lines (Table 1). Compound 1 demonstrated a similar value in mIMCD3 mouse epithelial cells ($IC_{50}$=5 nM) (Table 1).

Potency of Compound 1 Against cMet/HGFR Active Site Mutations in Cells c-Met/HGFR activating mutations have been identified in several human cancers and provide a strong rationale for proof of concept clinical studies based on both experimental evidence and clinical precedence with other RTK targets. Although c-Met/HGFR mutations in the extracellular or juxtamembrane domain are not predicted to affect compound binding to active site, it is possible that kinase domain mutations will cause loss of activity. To address this issue, RTK phosphorylation $IC_{50}$ was evaluated in compound 1 treated NIH3T3 cells engineered to express wild-type c-Met/HGFR or a series of representative c-Met/HGFR active-site mutations. In these studies, compound 1 exhibited improved or similar activity against ATP binding site mutants (V1092I, 19 nM and H1094R, 2.2 nM) or P-loop mutants (M1250T, 15 nM) compared with wild-type receptor (12.6 nM) (Table 1). Compound 1 also potently exhibited comparable potency inhibiting c-Met phosphorylation in NCI-H69 ($IC_{50}$: 13 nM) and HOP92 ($IC_{50}$: 16 nM) cells which express the endogenous c-Met juxtamembrane variants R988C and T1010I, respectively (Table 1). In contrast, a significant shift in potency (10-fold) was observed against the activation loop mutants (Y1230C, 127 nM and Y1235D, 92 nM) compared with wild type receptor (Table 1).

TABLE 1

| Assay | $IC_{50}$ nM | Selectivity Ratio[d] |
|---|---|---|
| Biochemical Activity In Vitro | | |
| c-Met/HGFR enzyme (Ki, nM)[a] | 4 | NA |
| Cellular Activity In Vitro | | |
| c-Met phosphorylation in human tumor cell lines (mean $IC_{50}$)[b,c] | 11 | NA |
| c-Met phosphorylation in mouse IMCD3 epithelial cells ($IC_{50}$)[b] | 5 | NA |
| Phosphorylation of c-Met WT in NIH3T3 cells ($IC_{50}$)[b] | 13 | NA |
| Phosphorylation of c-Met mutant V1092I in NIH3T3 cells ($IC_{50}$)[b] | 19 | NA |
| Phosphorylation of c-Met mutant H1094R in NIH3T3 cells ($IC_{50}$)[b] | 2 | 0.1X |
| Phosphorylation of c-Met mutant Y1230C in NIH3T3 cells ($IC_{50}$)[b] | 127 | 11X |
| Phosphorylation of c-Met mutant Y1235D in T47D cells ($IC_{50}$)[b] | 92 | 8X |
| Phosphorylation of c-Met mutant M1250T in NIH3T3 cells ($IC_{50}$)[b] | 15 | NA |
| Phosphorylation of c-Met in NCI-H69 cells expressing c-Met R988C variant ($IC_{50}$)[b] | 13 | NA |
| Phosphorylation of c-Met in HOP92 cells expressing c-Met T1010I variant ($IC_{50}$)[b] | 16 | NA |
| NPM-ALK phosphorylation in human Karpas299 lymphoma cells ($IC_{50}$)[b] | 24 | 2X |

TABLE 1-continued

| Assay | IC$_{50}$ nM | Selectivity Ratio[d] |
|---|---|---|
| Cellular Activity Against Non-Target Kinases In Vitro | | |
| MSP-stimulated RON phosphorylation in NIH-3T3-RON cells (mean IC$_{50}$)[b] | 189 | 17X |
| RON phosphorylation in RON-GYRB cells (mean IC$_{50}$)[b] | 298 | 27X |
| Gas6-stimulated Axl phosphorylation in NIH-3T3-Axl cells (mean IC$_{50}$)[b] | 322 | 29X |
| Ligand-stimulated Tie-2 phosphorylation in NIH-3T3-Tie-2/EGFR cells (mean IC$_{50}$)[b] | 448 | 41X |
| NGF-stimulated TrkA phosphorylation in Trk A-PAE cells (mean IC$_{50}$)[b] | 580 | 53X |
| BDNF-stimulated TrkB phosphorylation in Trk B-PAE cells (mean IC$_{50}$)[b] | 399 | 36X |
| BCR-Abl phosphorylation in BCR-Abl-BaF3 cells (mean IC$_{50}$)[b] | 1159 | >100X |
| Insulin-stimulated insulin receptor phosphorylation in 293-IRK cells (mean IC$_{50}$)[b] | 2887 | >250X |
| CD3-stimulated Lck-dependent Zap70 phosphorylation in Jurkat cells (mean IC$_{50}$)[b] | 2741 | >250X |
| Gas6-stimulated Sky phosphorylation in NIH-3T3-Sky cells (mean IC$_{50}$)[b] | >10000 | ~1000X |

Definitions
[a]Ki for c-Met/HGFR enzyme inhibition determined by monitoring NADH oxidation coupled to ATP turnover.
[b]IC$_{50}$ values were determined after exposure of various cell lines to several concentrations of PF-02341066 for 1 hour and measuring phosphorylation in cellular protein lysates by ELISA. IC$_{50}$ values were generated by curve fitting using a four-parameter analysis.
[c]Mean IC$_{50}$ value derived from mean IC$_{50}$ value for c-Met/HGFR phosphorylation across a panel of 7 human tumor cell lines (i.e., A549, MDA-MB-231, GTL-16, HT29, 786-O, Colo-205, A498).
[d]Mean [c]cell c-Met IC$_{50}$ was used to calculate the selectivity ratio for cell assays. Selectivity Index was calculated as IC$_{50}$, (c-Met)/IC$_{50}$, (target).
WT = Wild Type Effect of Compound 1 on c-Met/HGFR- or NPM-ALK-Dependent Oncogenic Phenotypes in Cells Phenotypic Assays c-Met/HGFR has been implicated in the dysregulation of cell growth, migration, and invasion of a variety of tumor cells and tumor endothelial cells while NPM-ALK is implicated in the dysregulation of cell proliferation and apoptosis in ALCL lymphoma cells. In a series of cell-based functional assays, compound 1 potently inhibited human GTL-16 gastric carcinoma cell growth, induced GTL-16 cell apoptosis, inhibited HGF-stimulated human NCI-H441 lung carcinoma cell migration and invasion through a matrigel matrix, and inhibited HGF-stimulated MDCK cell motility/scattering. (Table 2) Compound 1 also inhibited proliferation of Karpas 299 or SU-DHL-1 ALCL cells that express an NPM-ALK fusion protein due to a t2;5 chromosomal translocation. Growth inhibition by compound 1 in these NPM-ALK positive lymphoma cells was associated with G$_0$/G$_1$ cell cycle arrest and induction of apoptosis. To also investigate potential anti-angiogenic activity, compound 1 inhibited HGF-mediated HUVEC endothelial cell survival and matrigel invasion as well as HMVEC endothelial cell tubulogenesis in fibrin gels. These data demonstrate the ability of compound 1 to inhibit both c-Met/HGFR- and NPM-ALK-dependent functions in cells expressing activated c-Met/HGFR or NPM-ALK, respectively. In addition, these data suggest that anti-tumor efficacy of compound 1 may be mediated by both direct effects on tumor cell growth or survival as well as anti-angiogenic mechanisms.

TABLE 2

| | PF-02314066 Concentration | |
|---|---|---|
| Assay | nM | ng/mL |
| Tumor Cell Phenotypes | | |
| Proliferation (MTT assay) of GTL-16 gastric carcinoma cells (mean IC$_{50}$) | 9.7 | 4.4 |
| Apoptosis (ccDNA assay) of GTL-16 gastric carcinoma cells (mean IC$_{50}$) | 8.4 | 3.8 |
| HGF-stimulated NCI-H441 NSCLC cell Boyden Chamber migration (mean IC$_{50}$) | 11 | 5 |
| HGF-stimulated NCI-H441 NSCLC cell Matrigel invasion (mean IC$_{50}$) | 6.1 | 2.7 |
| HGF-stimulated MDCK cell colony scattering (mean IC$_{50}$) | 16 | 7 |
| Endothelial Cell Phenotypes | | |
| HGF-stimulated HUVEC endothelial cell survival (MTT assay) (mean IC$_{50}$) | 11 | 5 |
| HGF-stimulated HUVEC cell Matrigel invasion (mean IC$_{50}$) | 35 | 16 |
| HMVEC endothelial cell tubulogenesis in fibrin gels (estimated IC$_{50}$) | 80 | 36 |

Definitions:
NSCLC = non-small cell lung cancer; MDCK = Madin-Darby Canine Kidney; ALCL = anaplastic large cell lymphoma; HUVEC = human umbilical vein endothelial cells; HMVEC = human microvascular endothelial cells In-Vivo Studies Data and Results In Vivo Kinase Target Inhibition and Tumor Growth Inhibition Tumor Model Selection c-Met/HGFR-dependent tumor xenograft models were utilized to evaluate the relationship of c-Met/HGFR target inhibition, tumor growth inhibition, and plasma exposure of compound 1 in vivo. Due to lack of paracrine activation of human c-Met/HGFR expressed by tumor xenografts by mouse HGF expressed by mouse mesenchymal cells, human xenograft models exhibiting constitutive c-Met/HGFR activity were utilized as follows: 1) the GTL-16 human gastric carcinoma or Caki-1 renal carcinoma model that expresses elevated levels of constitutively active c-Met/HGFR, 2) the U87MG human glioblastoma or PC-3 human prostate carcinoma model that expresses both HGF and c-Met/HGFR comprising an autocrine loop, or 3) co-implantation of human tumor cells (e.g., NCI-H441 NSCLC) with human MRC5 fibroblasts to supply a source of bioactive human HGF from the tumor stromal compartment to restore species-specific paracrine activation of c-Met/HGFR.

Relationship of c-Met/HGFR Inhibition to Anti-Tumor Efficacy Following Oral Administration GTL-16 Tumors Athymic mice bearing established GTL-16 tumors (250 mm$^3$) were administered compound 1 orally at the indicated dose or vehicle alone for 11 days. For studies investigating inhibition of c-Met/HGFR phosphorylation in GTL-16 (FIG. 2A), mice were humanely euthanized at the end of study at designated time points post-administration, tumors were resected and frozen, and phosphorylation in vehicle and treated groups was quantitated by ELISA. Inhibition of kinase target phosphorylation by compound 1 in tumors was calculated as: % Inhibition=100−[(Mean OD treated/Mean OD untreated)×100]. For studies investigating GTL-16 tumor growth inhibition (FIG. 2B), tumor volume was measured by calipers on the indicated days with the median tumor volume±SEM indicated for groups of 15 mice. Percent (%) values shown are the % of tumor growth inhibition measured on day 20 for drug-treated compared to vehicle-treated mice and are calculated as: 100*{1−[(Treated Day 20−Treated Day 10)/(Control Day 20−Control Day 10)]}. An * denotes that the median tumor volumes are significantly less in the treated vs. the control group (P<0.001) as determined using one-way analysis of variance (See FIG. 2B).

Figure 2A:
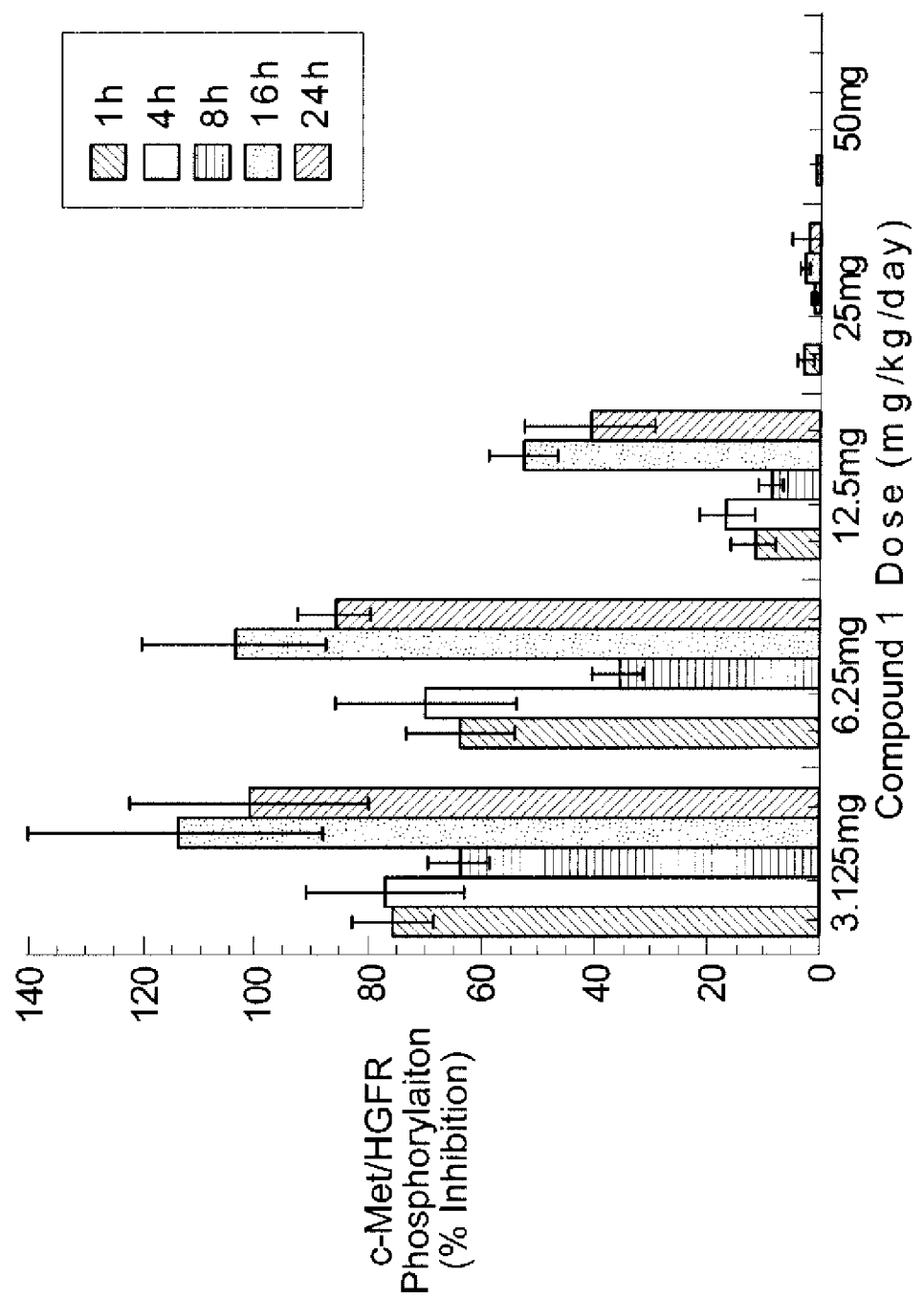
FIG. 2A: Studies investigating inhibition of c-Met/HGFR phosphorylation in GTL-16.
Figure 2B:
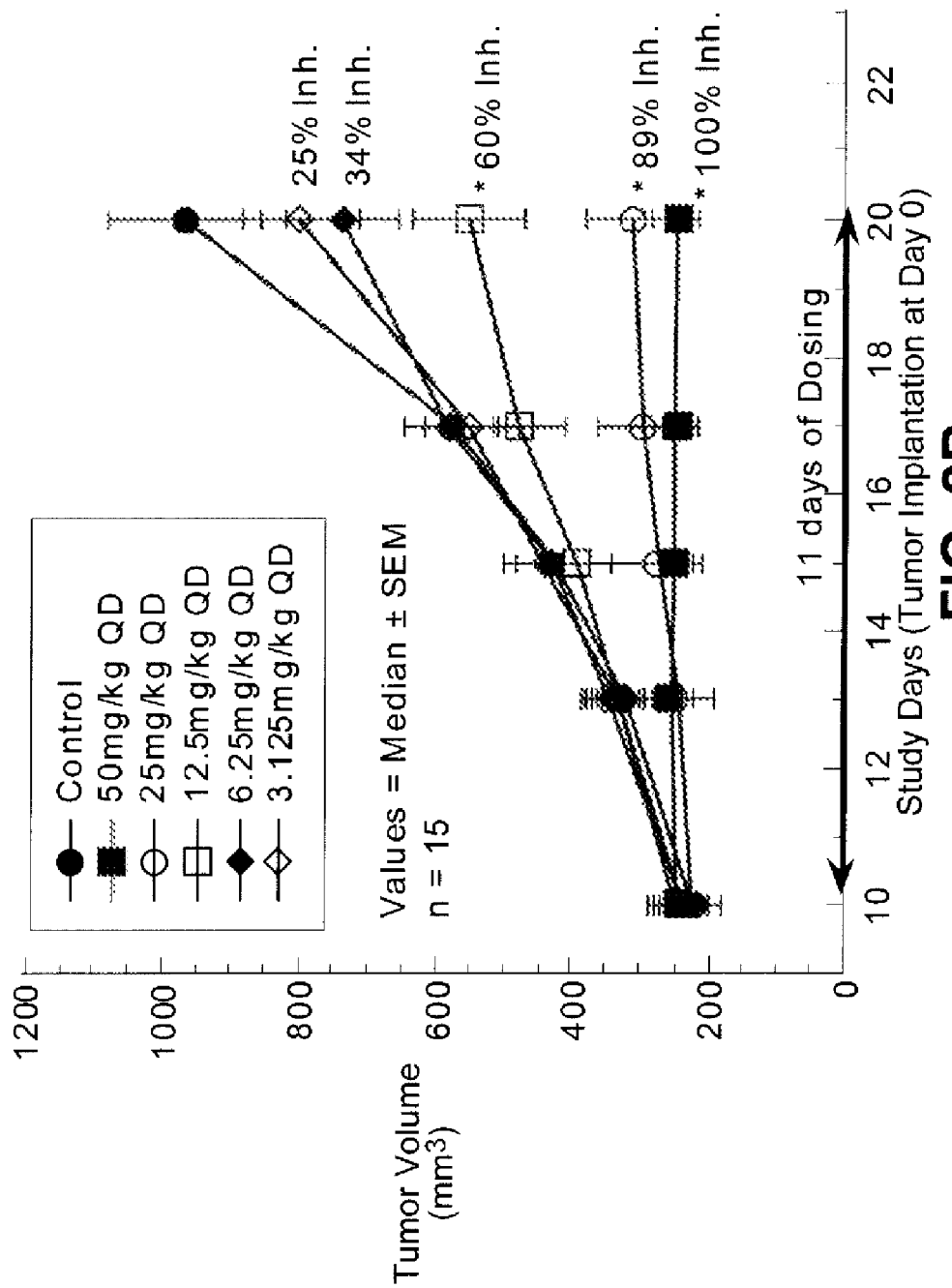
FIG. 2B: Studies investigating GTL-16 tumor growth inhibition.

To evaluate the c-Met/HGFR PD response to compound 1, GTL-16 tumors were harvested at several time points following oral administration of compound 1 in both single dose- and repeat-dose (steady state) studies. c-Met/HGFR phosphorylation status in tumors was quantitated by ELISA over a range of doses. With focus on steady-state PD studies (11-day) to draw a correlation with tumor growth inhibition, compound 1 demonstrated the following as shown in FIGS. 2A and 2B:

At 50 mg/kg/day: 100% tumor growth inhibition correlated with complete inhibition of c-Met/HGFR phosphorylation in GTL-16 tumors sustained for 24 hours (25 mg/kg—near complete inhibition of both phosphorylation and tumor growth). At 12.5 mg/kg/day: 60% tumor growth inhibition correlated with 80-90% inhibition of c-Met/HGFR phosphorylation at 1-8 hours which decreased to 50-60% inhibition by 16-24 hours.

At 6.25 mg/kg/day: non-significant trend toward tumor growth inhibition correlated with 30-50% inhibition of c-Met/HGFR phosphorylation at 1-8 hours with full recovery by 16 hours.

U87MG Tumors

Figure 3A:
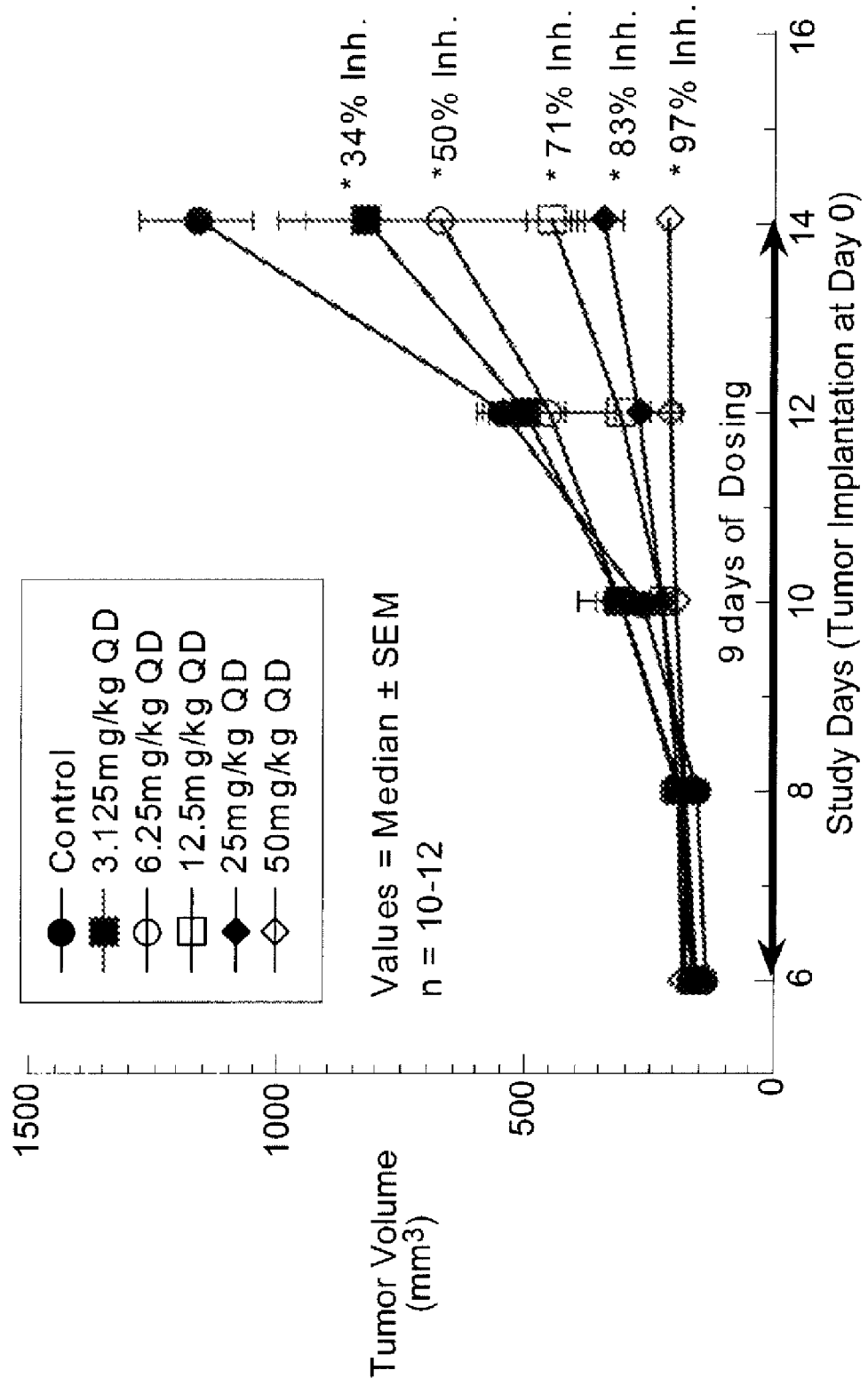
FIG. 3A: Studies investigating tumor growth inhibition.
Figure 3B:
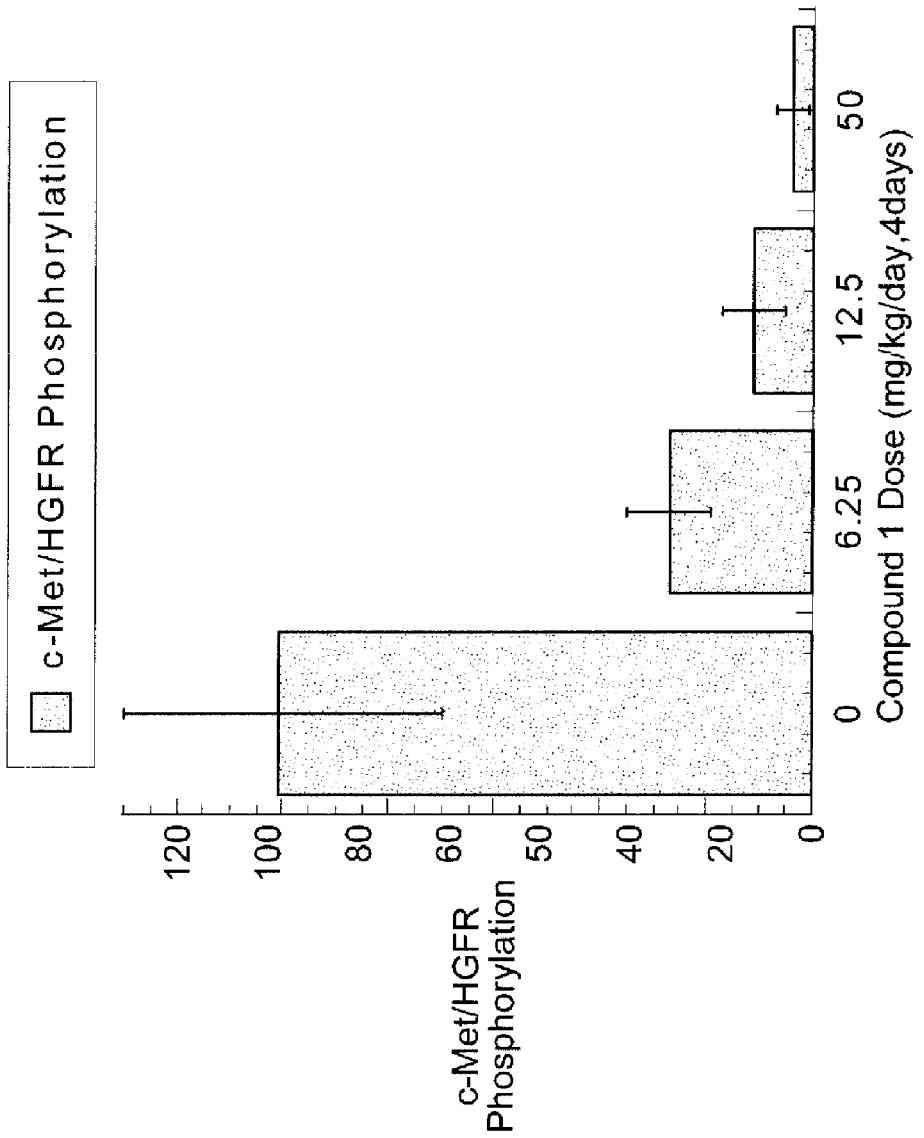
FIG. 3B: Studies investigating inhibition of c-Met/HGFR phosphorylation.

Athymic mice bearing established U87MG tumors (150 mm$^3$) were administered compound 1 orally at the indicated dose or vehicle alone for 9 days. For studies investigating tumor growth inhibition (FIG. 3A), tumor volume was measured by calipers on the indicated days with the median tumor volume±SEM indicated for groups of 10-12 mice. Percent (%) values shown are the % of tumor growth inhibition measured on day 14 for drug-treated compared to vehicle-treated mice and are calculated as: 100*{1−[(Treated Day 14−Treated Day 6)/(Control Day 14−Control Day 6)]}. An * denotes that the median tumor volumes are significantly less in the treated vs. the control group (P<0.001) as determined using one-way analysis of variance (See FIG. 3A). For studies investigating inhibition of c-Met/HGFR phosphorylation (FIG. 3B), mice were humanely euthanized at the end of study 4 hours post-administration of compound 1, tumors were resected and frozen, and phosphorylation in vehicle and treated groups was quantitated by ELISA. Inhibition of kinase target phosphorylation by compound 1 in tumors was calculated as: % Inhibition=100−[(Mean OD treated/Mean OD untreated)×100].

Pharmacologically relevant inhibition of Tie-2 phosphorylation was not observed in U87MG xenografts at dose levels up to 100 mg/kg suggesting that compound 1 was selective for its intended targets at similar dose levels.

Antitumor Efficacy of Compound 1 in Human Xenograft Models

The antitumor efficacy of compound 1 was evaluated in a variety of human tumor xenograft models representative of cancer indications in which dysregulation of c-Met/HGFR is implicated including GTL-16 gastric carcinoma, U87MG glioblastoma, NCI-H441 NSCLC, and PC-3 prostate carcinoma (Table 4).

GTL-16 Gastric Carcinoma Model

Figure 4A:
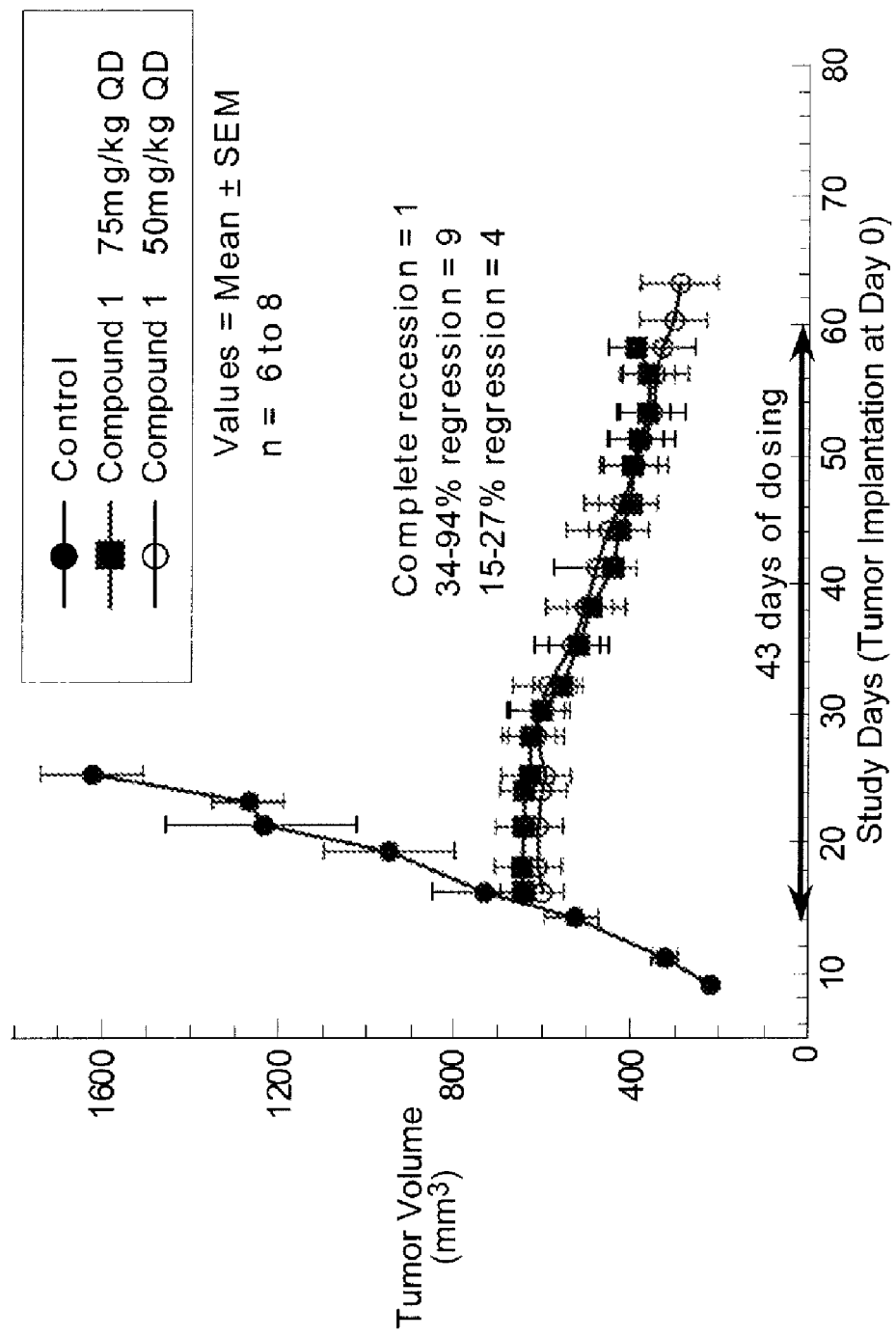
FIG. 4A: Regression of large established GTL-16 tumor xenografts in athymic mice.
Figure 4B:
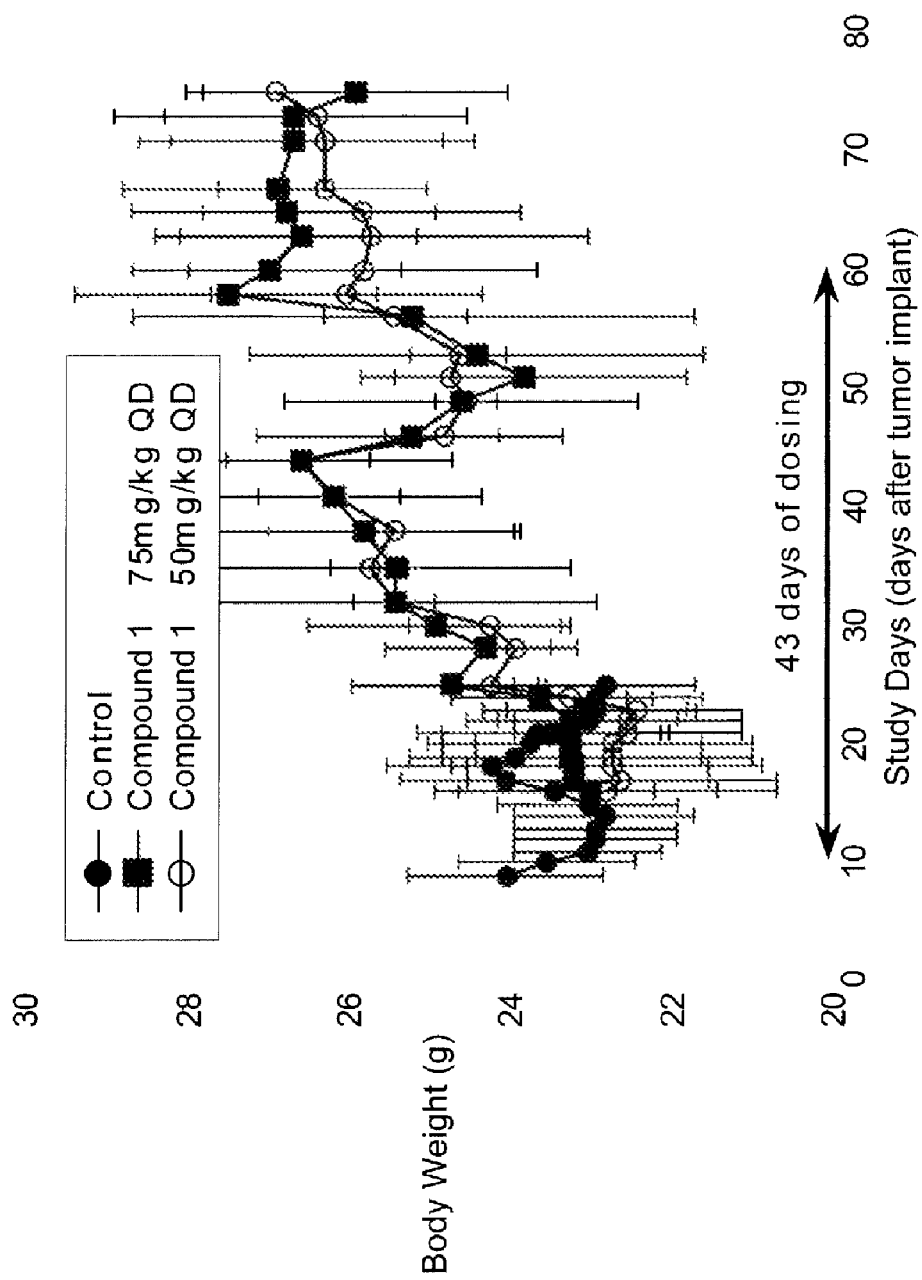
FIG. 4B: Mouse body weight following daily oral administration of compound 1.

Utilizing the GTL-16 gastric carcinoma model, compound 1 demonstrated the ability to cause marked regression of large established tumors (>600 mm$^3$) (FIG. 4). In this study, the 50 and 75 mg/kg/day compound 1 treatment cohorts exhibited equivalent mean tumor regression during the 43-day administration schedule, which provided further evidence that 50 mg/kg/day represents the maximally efficacious dose level. As illustrated in FIG. 4, the mean tumor regression at 50 or 75 mg/kg/day was 60% after 43 days of compound 1 administration. In the present study, each tumor decreased in mass during the 43-day compound 1 administration cycle at each dose level, with 9 of 14 mice exhibiting a ≧30% decrease in tumor mass (partial response), and one animal exhibiting a complete response with no evidence of tumor even after cessation of treatment for 10 days.

Regression of Large Established GTL-16 Tumor Xenografts in Athymic Mice (FIG. 4A) and Mouse Body Weight (FIG. 4B) Following Daily Oral Administration of compound 1. Athymic mice bearing established GTL-16 tumors (620 mm3) were administered compound 1 orally at the indicated dose levels or vehicle alone for 43 days. To investigate antitumor efficacy (FIG. 4A), tumor volume was measured by calipers on the indicated days with the median tumor volume±SEM indicated for groups of 6-8 mice. (FIG. 4B) Mean mouse weight in compound 1 treatment and vehicle control groups are illustrated in right hand panel.

NCI-H441 NSCLC model/Caki-1/PC-3 Tumor Xenografts

Athymic mice bearing established NCI-H441 (100 mm3) (FIG. 5A), Caki-1 (Table 3A, Table 3B) or PC-3 tumor xenografts (FIG. 5B) were administered compound 1 orally at the indicated dose or vehicle alone for 38, 40 or 20 days, respectively. Tumor volume was measured by calipers on the indicated days with the median tumor volume±SEM. An * denotes that the median tumor volumes are significantly less in the treated vs. the control group (P<0.001) as determined using one-way analysis of variance. (See FIG. 5).

Figure 5B:
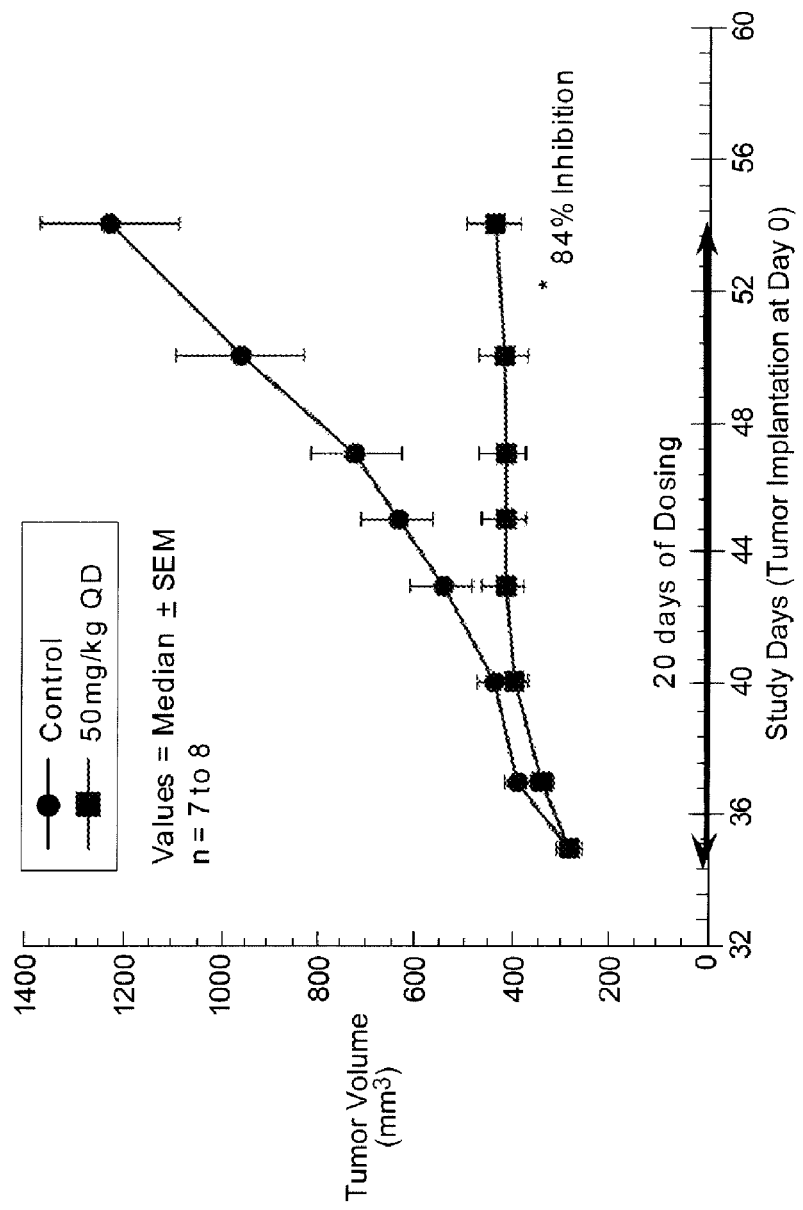
FIG. 5B: Tumor regression in athymic mice bearing established PC-3 tumor xenografts.

In NCI-H441 NSCLC model, a 43% mean regression of established tumors was observed at 50 mg/kg/day after 15 mg/kg/day (FIG. 5). The antitumor efficacy of compound 1 observed in the NCI-H441 model was consistent with the inhibition of c-Met/HGFR phosphorylation in tumors from compound treatment groups compared with vehicle treated controls. In the Caki-1 renal carcinoma model, a 53% decrease in mean tumor volume was observed at 50 mg/kg/day during the 33-day compound 1 administration cycle (FIG. 5B). In the Caki-1 study, each tumor decreased in volume by at least 30% during the 33-day compound 1 administration cycle (Table 3B, Table 4). Antitumor efficacy of compound 1 was also investigated in the PC-3 prostate carcinoma xenograft model and near complete inhibition of tumor growth (84% growth inhibition) was observed in this model.

TABLE 3A

Tumor Volume (mm³)
Control Subjects

| Day | 1 | 2 | 3 | 4 | 5 | 6 | 7 | 8 | 9 | 10 | Mean | SEM | n |
|---|---|---|---|---|---|---|---|---|---|---|---|---|---|
| 1  | 63  | 63   | 63  | 108 | 126  | 126 | 126 | 144  | 196 | 196  | 121   | 15.7  | 10 |
| 4  | 108 | 63   | 144 | 256 | 405  | 320 | 405 | 320  | 550 | 446  | 301.6 | 50.1  | 10 |
| 8  | 108 | 144  | 196 | 256 | 936  | 405 | 726 | 446  | 1268| 700  | 518.4 | 120.7 | 10 |
| 12 | 126 | 365  | 196 | 256 | 1688 | 726 | 936 | 1008 |     | 1437 | 748.5 | 187.9 | 9  |
| 15 | 196 | 550  | 352 | 365 |      | 1008| 1372|      |     |      | 640.4 | 185.8 | 6  |
| 19 | 172 | 864  | 256 | 486 |      |     |     |      |     |      | 444.4 | 154.9 | 4  |
| 22 | 288 | 936  | 288 | 726 |      |     |     |      |     |      | 559.5 | 162.5 | 4  |
| 26 | 288 | 1268 | 365 | 650 |      |     |     |      |     |      | 642.5 | 222.4 | 4  |
| 29 | 221 |      | 405 | 1008|      |     |     |      |     |      | 544.5 | 237.8 | 3  |
| 33 | 320 |      | 550 |     |      |     |     |      |     |      | 435   | 115   | 2  |
| 36 | 405 |      | 550 |     |      |     |     |      |     |      | 477.5 | 72.5  | 2  |
| 40 | 486 |      | 600 |     |      |     |     |      |     |      | 543   | 57    | 2  |
| 43 | 726 |      | 864 |     |      |     |     |      |     |      | 795   | 69    | 2  |
| 47 | 787 |      | 936 |     |      |     |     |      |     |      | 861.3 | 74.8  | 2  |
| 50 | 787 |      | 1008|     |      |     |     |      |     |      | 897.3 | 110.8 | 2  |
| 54 | 787 |      |     |     |      |     |     |      |     |      | 786.5 |       | 1  |

TABLE 3B

Tumor Volume (mm³)
Experimental Subjects (Compound 1, 50 mg/kg)

| Day | 1 | 2 | 3 | 4 | 5 | 6 | 7 | 8 | 9 | 10 | Mean | SEM | n |
|---|---|---|---|---|---|---|---|---|---|---|---|---|---|
| 1  | 63 | 63 | 63 | 108 | 108 | 126 | 126 | 172 | 172 | 196 | 119.5 | 15.4 | 10 |
| 4  | 32 | 63 | 63 | 108 | 108 | 196 | 126 | 126 | 172 | 196 | 118.9 | 17.9 | 10 |
| 8  | 18 | 40 | 14 | 40  | 32  | 75  | 40  | 63  | 63  | 75  | 45.9  | 7    | 10 |
| 12 | 14 | 32 | 14 | 32  | 32  | 63  | 40  | 40  | 40  | 63  | 36.8  | 5.3  | 10 |
| 15 | 4  | 14 | 14 | 32  | 32  | 40  | 32  | 40  | 40  | 40  | 28.7  | 4.2  | 10 |
| 19 | 14 | 18 | 14 | 32  | 32  | 40  | 18  | 32  | 63  | 63  | 32.4  | 5.8  | 10 |
| 22 | 14 | 14 | 14 | 14  | 32  | 63  | 14  | 32  | 108 | 108 | 41    | 12.2 | 10 |
| 26 | 14 | 14 | 14 | 18  | 32  | 40  | 32  | 63  | 75  | 75  | 37.5  | 7.9  | 10 |
| 29 | 14 | 32 | 18 | 32  | 63  | 40  | 40  | 108 | 108 | 108 | 56.2  | 12   | 10 |
| 33 | 14 | 32 | 18 | 32  | 63  | 40  | 40  | 108 | 108 | 108 | 56.2  | 12   | 10 |
| 36 | 32 | 40 | 32 | 63  | 75  | 75  | 63  | 75  | 126 | 126 | 70.6  | 10.7 | 10 |
| 40 | 32 | 63 | 32 | 63  | 75  | 75  | 63  | 75  | 172 | 172 | 82    | 15.7 | 10 |
| 43 | 32 | 32 | 14 | 63  | 63  | 63  | 32  | 63  | 256 | 63  | 67.8  | 21.7 | 10 |
| 47 | 32 | 40 | 32 | 63  | 75  | 108 | 63  | 75  | 196 | 108 | 79.1  | 15.6 | 10 |
| 50 | 32 | 63 | 40 | 63  | 108 | 108 | 63  | 108 | 196 | 172 | 95.1  | 17.2 | 10 |
| 54 | 63 | 63 | 40 | 14  | 108 | 75  | 40  | 75  | 172 | 172 | 82    | 16.9 | 10 |

38-day of compound 1 administration (FIG. 5). In this study, each tumor decreased in mass during the 33-day compound 1 administration cycle at 50 mg/kg/day, with 3 of 11 mice exhibiting a ≧30% decrease in tumor mass (partial response), and 3 animals exhibiting a complete response with no evidence of tumor (FIG. 5). The antitumor efficacy of compound 1 was dose-dependent with regression of established NCI-H441 tumors observed at 50 mg/kg/day and partial inhibition of tumor growth (57% tumor growth inhibition) observed at Relationship of Antitumor Efficacy to Inhibition of c-Met/HGFR A series of dose-response antitumor efficacy and pharmacodynamic studies were performed to demonstrate the relationship between c-Met/HGFR target inhibition to antitumor efficacy. To evaluate the pharmacodynamic inhibition of c-Met/HGFR by compound 1, GTL-16 gastric carcinoma tumors were harvested at several time points following oral administration of compound 1. c-Met/HGFR phosphorylation status in tumors was quantitated by ELISA over a range of doses. In these studies, compound 1 demonstrated a strong correlation of dose- and time-dependent inhibition of c-Met/HGFR to inhibition of tumor growth. When defining the relationship of target PD to efficacy in the GTL-16 model the following conclusions were apparent 1) complete inhibition of c-Met/HGFR activity for 24 hours is consistent with complete inhibition of tumor growth (50 mg/kg, 100% TGI), 2) potent inhibition of c-Met/HGFR activity for only a portion of the schedule is consistent with suboptimal efficacy (12.5 mg/kg, 60% TGI), 3) inability to achieve >50% inhibition of c-Met/HGFR activity (3.125, 6.25 mg/kg) is consistent with lack of significant tumor growth inhibition (TGI) (FIGS. 2A and 2B). An additional GTL-16 study demonstrated that the 50 and 75 mg/kg/day compound 1 treatment cohorts exhibited equivalent mean tumor regression which provided further evidence that 50 mg/kg/day represents the maximally efficacious dose level (FIG. 4 and Table 4). These findings suggest that the duration of c-Met/HGFR inhibition is directly linked to anti-tumor efficacy of compound 1.

Furthermore, a similar dose-dose dependent effect of compound 1 on tumor growth and c-Met/HGFR phosphorylation was observed utilizing all tumor models (GTL-16, U87MG, and NCI-H441) and dosing schedules further these supporting observations (Table 4). In each of these studies the 50 mg/kg/day dose level resulted in either complete tumor growth inhibition or tumor regression (Table 4). In addition, a dose-dependent correlation was observed between inhibition of c-Met/HGFR phosphorylation and antitumor efficacy in each model further supporting the concept of maximizing of the extent and duration of c-Met/HGFR inhibition to achieve full efficacy. Collectively, these studies suggest that near-complete inhibition of c-Met/HGFR phosphorylation for the duration of the administration schedule is necessary to maximize therapeutic benefit and the extent and duration of the inhibition c-Met/HGFR activity was directly linked to the level of anti-tumor efficacy. This data supports the link between inhibition of the intended pharmacologic target of compound 1, c-Met/HGFR, and the degree of antitumor efficacy.

Antitumor Efficacy of Compound 1 in an NPM-ALK-Dependent Lymphoma Model

Karpas 299 ALCL Model

SCID-beige mice bearing established Karpas 299 tumors (220 mm$^3$) were administered compound 1 orally at the indicated dose or vehicle alone for designated time periods. For studies investigating tumor growth inhibition (FIG. 6A), tumor volume was measured by calipers on the indicated days with the median tumor volume±SEM indicated for groups of 8-12 mice. Percent (%) values shown are the % of tumor growth inhibition measured on day 23 for drug-treated compared to vehicle-treated mice and are calculated as: 100*{1−[(Treated Day 23−Treated Day 12)/(Control Day 23−Control Day 12)]}. An * denotes that the median tumor volumes are significantly less in the treated vs. the control group (P<0.001) as determined using one-way analysis of variance. For studies investigating inhibition of NPM-ALK phosphorylation (FIG. 6B), mice were humanely euthanized at the end of study 4 hours post-administration of compound 1, tumors were resected and frozen, and ALK phosphorylation in vehicle and treated tumors was quantitated by ELISA. Inhibition of kinase target phosphorylation by compound 1 in tumors was calculated as: % Inhibition=100−[(Mean OD treated/Mean OD untreated)×100].

Figure 6A:
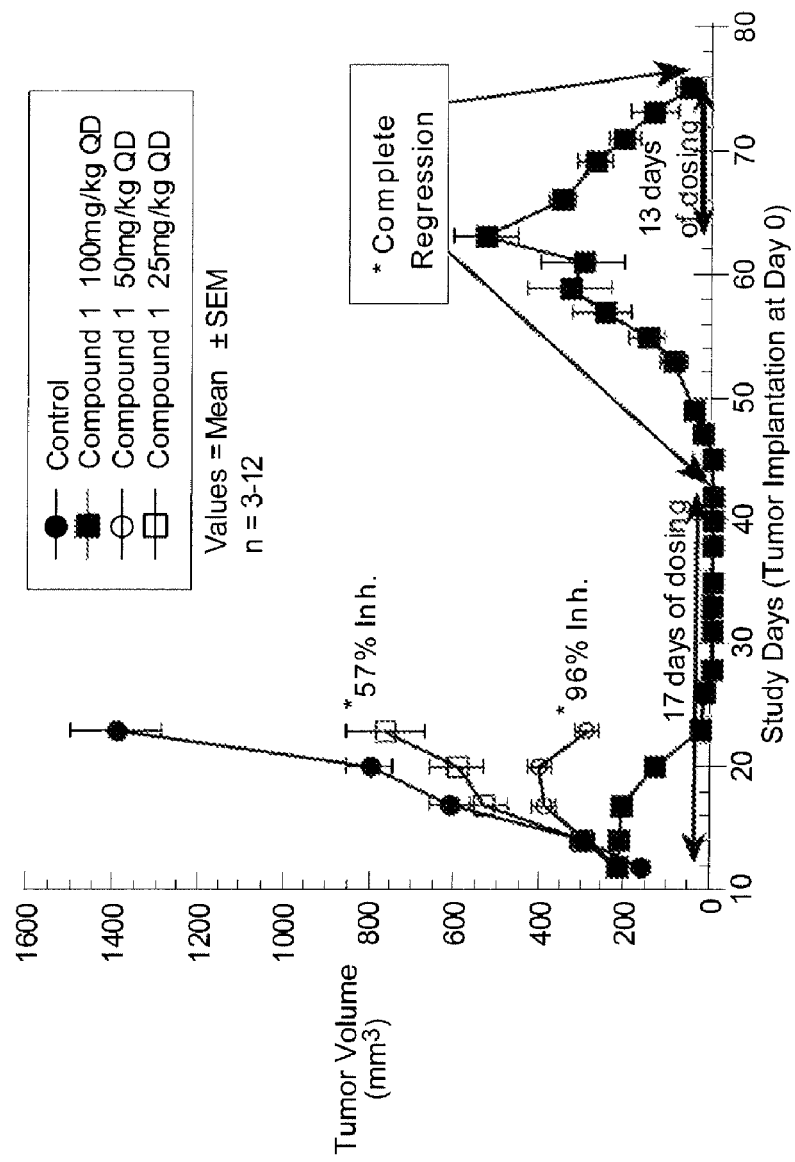
FIG. 6A: Studies investigating tumor growth inhibition.
Figure 6B:
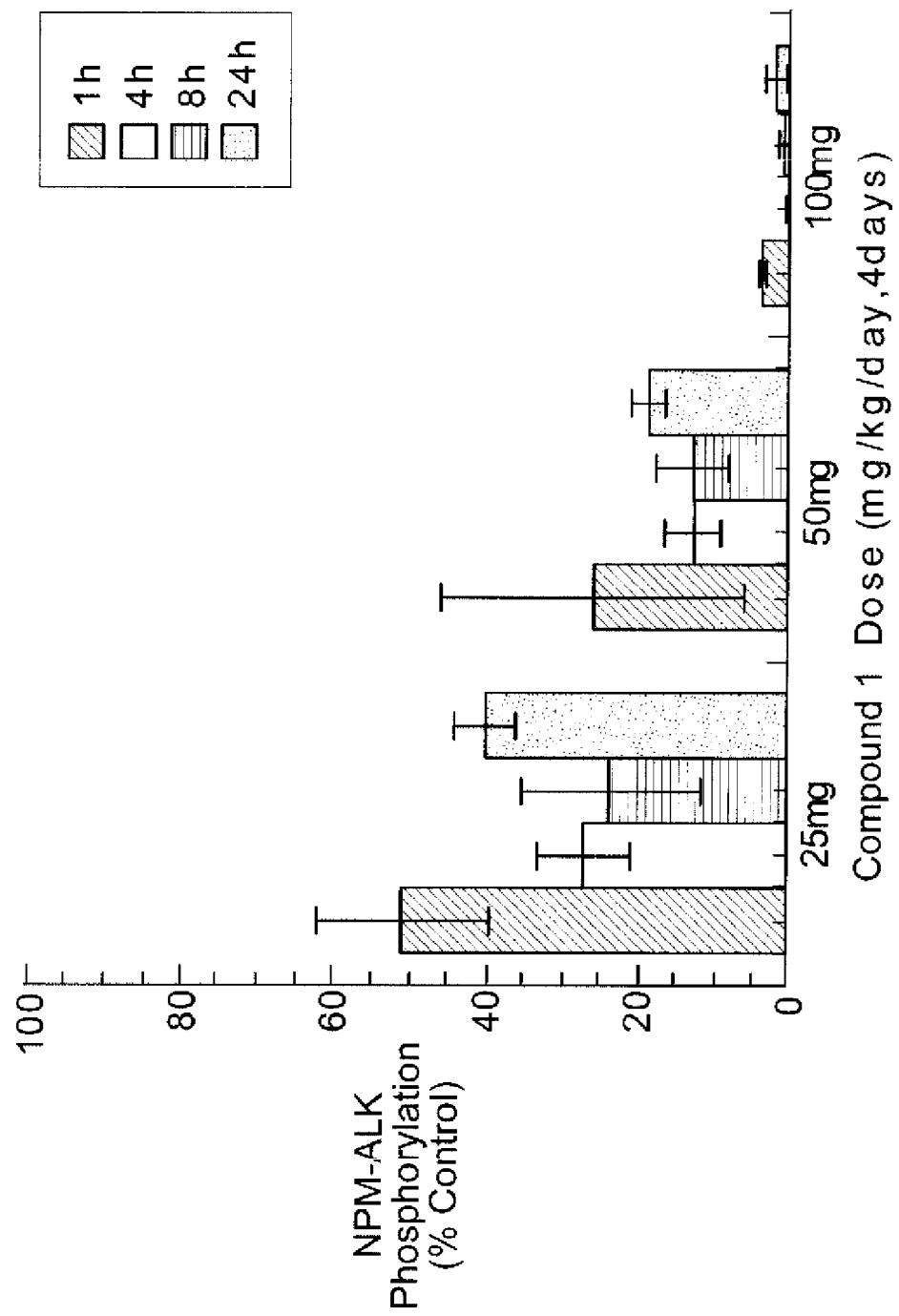
FIG. 6B: studies investigating inhibition of NPM-ALK phosphorylation.

Utilizing the Karpas 299 ALCL model, compound 1 demonstrated the ability to cause marked regression of established tumors (>200 mm$^3$) (FIG. 6A). In this study, the administration of compound 1 at 100 mg/kg/day resulted in complete regression of tumors of all mice in this dosing cohort within 15 days of the initiation compound administration (FIG. 6A). After 17 days compound 1 treatment was stopped resulting in tumor re-growth. When tumors grew to a larger size (>600 mm$^3$), compound 1 treatment was reinitiated for an additional 13 days and complete regression of tumors was demonstrated once again (FIG. 6A, Table 4). The cytoreductive effect of compound 1 is consistent with the observation of its anti-proliferative and apoptotic effects against ALCL cells in-vitro. The relationship of inhibition of tumor NPM-ALK phosphorylation to antitumor efficacy was also determined at multiple dose levels and time points. Similar to observations in c-Met/HGFR-dependent tumor models, near complete inhibition (>90% inhibition) of NPM-ALK activity for the full dosing interval (24 hours) is consistent with maximal antitumor efficacy (complete regression) at 100 mg/kg (FIGS. 6A and 6B). Incomplete inhibition of NPM-ALK phosphorylation (<90% inhibition at 25 or 50 mg/kg) is consistent with submaximal antitumor efficacy (FIGS. 6A and 6B). Similar to studies in c-Met/HGFR-dependent tumor models, this data supports the link between inhibition of the other intended pharmacologic target of compound 1, NPM-ALK, and the degree of antitumor efficacy in a NPM-ALK-dependent tumor model.

TABLE 4

| Model (Tumor Type) | Initial Tumor Volume (mm$^3$) | Dose & Schedule (mg/kg) | Overall Effect | | | | |
|---|---|---|---|---|---|---|---|
| | | | Growth Inh. % (Day)[1] | Regression[2] | PR | CR | P Value Vs |
| GTL-16 (Gastric Carcinoma) | 230 | 50, QD | 100% (d11) | No | 2/15 | No | <0.0001 |
| | 230 | 25, QD | 89% (d11) | No | No | No | <0.0001 |
| | 230 | 12.5, QD | 60% (d11) | No | No | No | 0.0013 |
| | 230 | 6.25, QD | 34% (d11) | No | No | No | 0.074 |
| | 230 | 3.125, QD | 29% (d11) | No | No | No | 0.144 |
| | 230 | 25, BID | 95% (d11) | No | No | No | <0.0001 |
| | 230 | 12.5, BID | 84% (d11) | No | No | No | <0.0001 |
| | 230 | 6.25, BID | 63% (d11) | No | No | No | <0.0001 |
| GTL-16 (Gastric Carcinoma) | 620 | 75, QD | Regression | 60% (d43) | 6/8 | No | <0.0001 |
| | 620 | 50, QD | Regression | 60% (d43) | 3/6 | 1/6 | <0.0001 |

TABLE 4-continued

| Model (Tumor Type) | Initial Tumor Volume (mm³) | Dose & Schedule (mg/kg) | Overall Effect | | | | P Value Vs |
|---|---|---|---|---|---|---|---|
| | | | Growth Inh. % (Day)[1] | Regression[2] | PR | CR | |
| U87 MG (Glioblastoma) | 170 | 50, QD | 97% (d9) | No | 1/12 | No | <0.0001 |
| | 170 | 25, QD | 83% (d9) | No | 1/12 | No | <0.0001 |
| | 170 | 12.5, QD | 71% (d9) | No | No | No | <0.0001 |
| | 170 | 6.25, QD | 50% (d9) | No | No | No | 0.0003 |
| | 170 | 3.125, QD | 34% (d9) | No | No | No | 0.0454 |
| H441 (NSCLC) | 100 | 50, QD | Regression | 48% (d38) | 3/11 | 3/11 | <0.0001 |
| | 100 | 15, QD | 59% (d9) | No | No | 2/12 | 0.0013 |
| PC-3 (Prostate Carcinoma) | 290 | 50, QD | 84% (d20) | No | No | No | 0.001 |
| Caki-1 (Renal Carcinoma) | 100 | 50, QD | Regression | 53% | 7/10 | 3/10 | 0.001 |
| Karpas 299 (ALK lymphoma) | 220 | 100, QD | Regression | 100% (d16) | No | 12/12 | <0.0001 |
| | 220 | 50, QD | 96% (d11) | No | No | No | <0.0001 |
| | 220 | 25, QD | 57% (d11) | No | No | No | <0.0001 |
| | 540 | 100, QD | Regression | 90% (d13) | 3/3 | No | <0.0001 |

Synthesis of Compound 1

PLE is an enzyme produced by Roche and sold through Biocatalytics Inc. as a crude esterase preparation from pig liver, commonly known as PLE-AS (purchased from Biocatalytics as ICR-123, sold as an ammonium sulfate suspension). The enzyme is classified in the CAS registry as a "carboxylic-ester hydrolase, CAS no. 9016-18-6". The corresponding enzyme classification number is EC 3.1.1.1. The enzyme is known to have broad substrate specificity towards the hydrolysis of a wide range of esters. The lipase activity is determined using a method based on hydrolysis of ethyl butyrate in a pH titrator. 1 LU (lipase unit) is the amount of enzyme which liberates 1 µmol titratable butyric acid per minute at 22° C., pH 8.2. The preparation reported herein (PLE-AS, as a suspension) is usually shipped as an opaque brown-green liquid with a declared activity of >45 LU/mg (protein content around 40 mg/mL).

(1S)-1-(2,6-dichloro-3-fluorophenyl)ethanol (1S)-1-(2,6-dichloro-3-fluorophenyl)ethanol, shown as compound (S-1) in the schemes below, was prepared by a combination of enzymatic hydrolysis of racemic 1-(2,6-dichloro-3-fluorophenyl)ethyl acetate, esterification and chemical hydrolysis with inversion according to Scheme B. Racemic 1-(2,6-dichloro-3-fluorophenyl)ethyl acetate (compound A2) was prepared according to Scheme A.

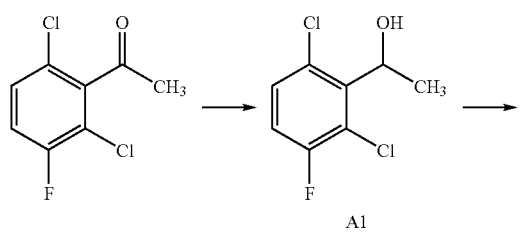

Scheme A

-continued

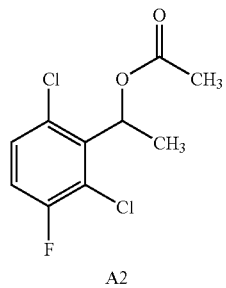

A2

1-(2,6-dichloro-3-fluorophenyl)ethanol (A1): Sodium borohydride (90 mg, 2.4 mmol) was added to a solution of 2',6'-dichloro-3'-fluoro-acetophenone (Aldrich, catalog #52, 294-5) (207 mg, 1 mmol) in 2 mL of anhydrous CH₃OH. The reaction mixture was stirred at room temperature for 1 h then was evaporated to give a colorless oil residue. The residue was purified by flash chromatography (eluting with 0→10% EtOAc in hexanes) to give compound A1 as a colorless oil (180 mg; 0.88 mmol; 86.5% yield); MS (APCI) (M-H)⁻ 208; 1H NMR (400 MHz, chloroform-D) δ ppm 1.64 (d, J=6.82 Hz, 3H) 3.02 (d, J=9.85 Hz, 1H) 6.97-7.07 (m, 1H) 7.19-7.33 (m, 1H).

1-(2,6-dichloro-3-fluorophenyl)ethyl acetate (A2): Acetic anhydride (1.42 mL, 15 mmol) and pyridine (1.7 mL, 21 mmol) were added sequentially to a solution of compound A1 (2.2 g, 10.5 mmol) in 20 mL of CH₂Cl₂. The reaction mixture was stirred at room temperature for 12 h and then evaporated to give a yellowish oil residue. The residue was purified by flash chromatography (eluting with 7→9% EtOAc in hexanes) to give compound A2 as a colorless oil (2.26 g; 9.0 mmol; 85.6% yield); 1H NMR (400 MHz, chloroform-D) δ ppm 1.88 (d, J=6.82 Hz, 3 H) 2.31 (s, 3H) 6.62 (q, J=6.82 Hz, 1H) 7.25 (t, J=8.46 Hz, 1H) 7.49 (dd, J=8.84, 5.05 Hz, 1H).

Scheme B

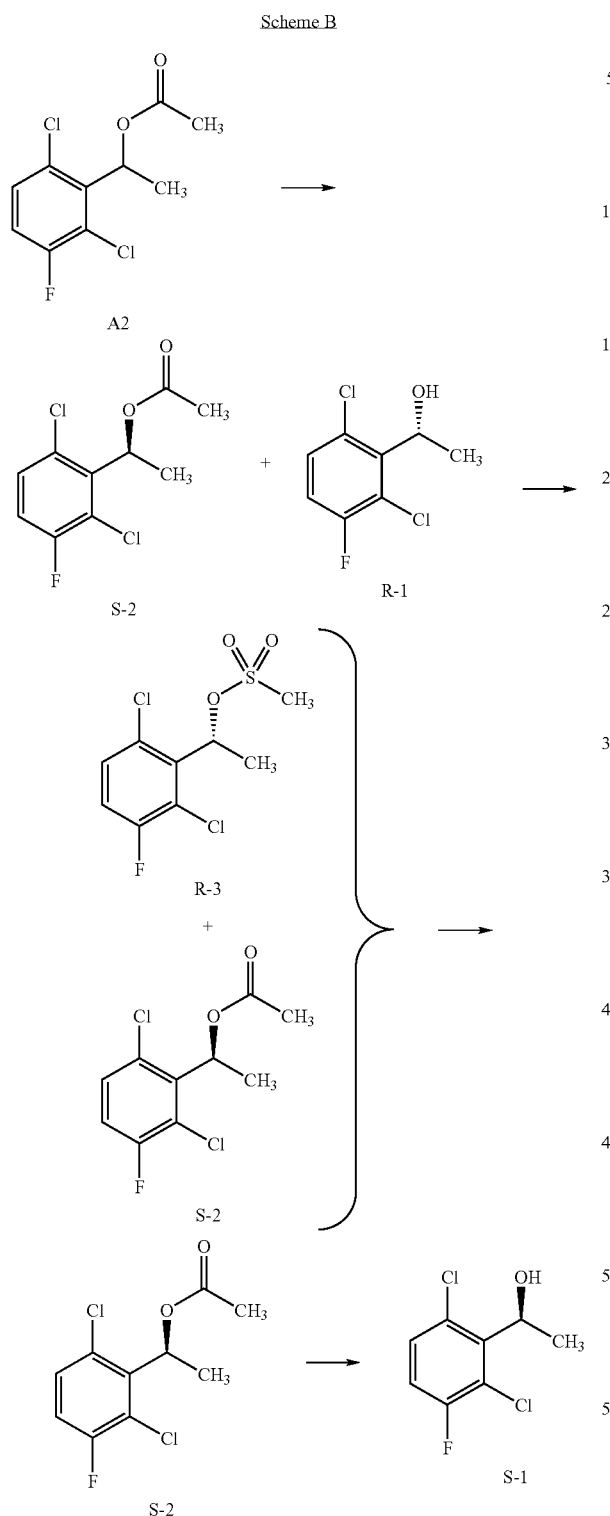

To a 50 mL jacketed flask equipped with a pH electrode, an overhead stirrer and a base addition line (1M NaOH), was added 1.2 mL of 100 mM potassium phosphate buffer pH 7.0 and 0.13 mL of PLE AS suspension. Then, compound A2 (0.13 g, 0.5 mmol, 1.00 eq) was added dropwise and the resulting mixture was stirred at room temperature for 20 h, maintaining the pH of the reaction constant at 7.0 using 1 M NaOH. Both the conversion and ee's of the reaction were monitored by RP-HPLC, and stopped after 50% starting material was consumed (approximately 17 hours under these conditions). The mixture was then extracted three times with 10 mL of ethyl acetate to recover both ester and alcohol as a mixture of R-1 and S-2.

Methanesulfonyl chloride (0.06 mL, 0.6 mmol) was added to a solution of a mixture of R-1 and S-2 (0.48 mmol) in 4 mL of pyridine under nitrogen atmosphere. The reaction mixture was stirred at room temperature for 3 h then evaporated to obtain an oil. Water (20 mL) was added to the mixture and then EtOAc (20 mL×2) was added to extract the aqueous solution. The organic layers were combined, dried, filtered, and evaporated to give a mixture of R-3 and S-2. This mixture was used in the next step reaction without further purification. $^1$H NMR (400 MHz, chloroform-D) δ ppm 1.66 (d, J=7.1 Hz, 3H) 1.84 (d, J=7.1 Hz, 3H) 2.09 (s, 3H) 2.92 (s, 3H) 6.39 (q, J=7.0 Hz, 1H) 6.46 (q, J=6.8 Hz, 1H) 6.98-7.07 (m, 1H) 7.07-7.17 (m, 1H) 7.23-7.30 (m, 1H) 7.34 (dd, J=8.8, 4.80 Hz, 1H).

Potassium acetate (0.027 g, 0.26 mmol) was added to a mixture of R-3 and S-2 (0.48 mmol) in 4 mL of DMF under nitrogen atmosphere. The reaction mixture was heated to 100° C. for 12 h. Water (20 mL) was added to the reaction mixture and EtOAc (20 mL×2) was added to extract the aqueous solution. The combined organic layer was dried, filtered, and evaporated to give an oil of S-2 (72 mg, 61% yield in two steps). Chirality ee: 97.6%. $^1$H NMR (400 MHz, chloroform-D) δ ppm 1.66 (d, J=7.1 Hz, 3H) 2.09 (s, 3H) 6.39 (q, J=6.8 Hz, 1H) 7.02 (t, J=8.5 Hz, 1H) 7.22-7.30 (m, 1H).

Sodium methoxide (19 mmol; 0.5 M in methanol) was added slowly to compound S-2 (4.64 g, 18.8 mmol) under a nitrogen atmosphere at 0° C. The resulting mixture was stirred at room temperature for 4 hours. The solvent was evaporated and H$_2$O (100 mL) was added. The cooled reaction mixture was neutralized with sodium acetate-acetic acid buffer solution to pH 7. Ethyl acetate (100 mL×2) was added to extract the aqueous solution. The combined organic layers were dried over Na$_2$SO$_4$, filtered, and evaporated to obtain S-1 as a white solid (4.36 g, 94.9% yield); SFC-MS: 97% ee. $^1$H NMR (400 MHz, chloroform-D) δ ppm 1.65 (d, J=6.8 Hz, 3 H) 5.58 (q, J=6.9 Hz, 1H) 6.96-7.10 (m, 1H) 7.22-7.36 (m, 1H).

5-bromo-3-[1-(2,6-dichloro-3-fluoro-phenyl)-ethoxy]-pyridin-2-ylamine (racemate)

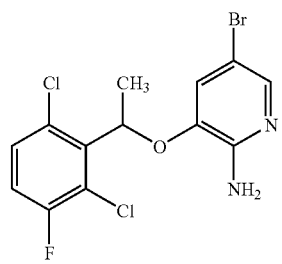

1. 2,6-Dichloro-3-fluoroacetophenone (15 g, 0.072 mol) was stirred in THF (150 mL, 0.5M) at 0° C. using an ice bath for 10 min. Lithium aluminum hydride (2.75 g, 0.072 mol) was slowly added. The reaction was stirred at ambient temperature for 3 hr. The reaction was cooled in ice bath, and water (3 mL) was added drop wisely followed by adding 15% NaOH (3 mL) slowly. The mixture was stirred at ambient temperature for 30 min. 15% NaOH (9 mL), MgSO$_4$ were added and the mixture filtered to remove solids. The solids were washed with THF (50 mL) and the filtrate was concentrated to give 1-(2,6-dichloro-3-fluoro-phenyl)-ethanol (14.8 gm, 95% yield) as a yellow oil. $^1$H NMR (400 MHz, DMSO-d$_6$) δ 1.45 (d, 3H), 5.42 (m, 2H), 7.32 (m, 1H), 7.42 (m, 1H).

2. To a stirred solution of triphenyl phosphine (8.2 g, 0.03 mol) and DEAD (13.65 mL of a 40% solution in toluene) in THF (200 mL) at 0° C. was added a solution of 1-(2,6-dichloro-3-fluoro-phenyl)-ethanol (4.55 g, 0.021 mol) and 3-hydroxy-nitropyridine (3.35 g, 0.023 mol) in THF (200 mL). The resulting bright orange solution was stirred under a nitrogen atmosphere at ambient temperature for 4 hours at which point all starting materials had been consumed. The solvent was removed, and the crude material was dry loaded onto silica gel, and eluted with ethyl acetate-hexanes (20:80) to yield 3-(2,6-dichloro-3-fluoro-benzyloxy)-2-nitro-pyridine (6.21 g, 0.021 mol, 98%) as a pink solid. $^1$H NMR (CDCl$_3$, 300 MHz) δ 1.8-1.85 (d, 3H), 6.0-6.15 (q, 1H), 7.0-7.1 (t, 1H), 7.2-7.21 (d, 1H), 7.25-7.5 (m, 2H), 8.0-8.05 (d, 1H).

3. To a stirred mixture of AcOH (650 mL) and EtOH (500 mL) was suspended 3-(2,6-dichloro-3-fluoro-benzyloxy)-2-nitro-pyridine (9.43 g, 0.028 mol) and iron chips (15.7 g, 0.28 mol). The reaction was heated slowly to reflux and allowed to stir for 1 hr. The reaction was cooled to room temperature then diethyl ether (500 mL) and water (500 mL) was added. The solution was carefully neutralized by the addition of sodium carbonate. The combined organic extracts were washed with sat'd NaHCO$_3$ (2×100 mL), H$_2$O (2×100 mL) and brine (1×100 mL) then dried (Na$_2$SO$_4$), filtered and concentrated to dryness under vacuum to yield 3-(2,6-dichloro-3-fluoro-benzyloxy)-pyridin-2-ylamine (9.04 g, 0.027 mol, 99%) as a light pink solid. $^1$H NMR (CDCl$_3$, 300 MHz) δ 1.8-1.85 (d, 3H), 4.9-5.2 (brs, 2H), 6.7-6.84 (q, 1H), 7.0-7.1 (m, 1H), 7.2-7.3 (m, 1H), 7.6-7.7 (m, 1H).

4. A stirring solution of 3-(2,6-dichloro-3-fluoro-benzyloxy)-pyridin-2-ylamine (9.07 g, 0.03 mol) in acetonitrile was cooled to 0° C. using an ice bath. To this solution was added N-bromosuccinimide (NBS) (5.33 g, 0.03 mol) portionwise. The reaction was stirred at 0° C. for 15 min. The reaction was concentrated to dryness under vacuum. The resulting dark oil was dissolved in EtOAc (500 mL), and purified via silica gel chromatography. The solvents were then removed in vacuo to yield 5-bromo-3-(2,6-dichloro-3-fluoro-benzyloxy)-pyridin-2-ylamine (5.8 g, 0.015 mol, 51%) as a white crystalline solid. $^1$H NMR (CDCl$_3$, 300 MHz) δ 1.85-1.95 (d, 3H), 4.7-5.0 (brs, 2H), 5.9-6.01 (q, 1H), 6.8-6.95 (d, 1H), 7.01-7.2 (t, 1H), 7.4-7.45 (m, 1H), 7.8-7.85 (d, 1H).

5-bromo-3-[1(R)-(2,6-dichloro-3-fluoro-phenyl)-ethoxy]-pyridin-2-ylamine

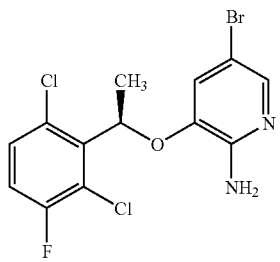

The enantiomerically pure R isomer was prepared as described above for the racemate, but using the enantiomerically pure starting materials described above. $^1$H NMR (400 MHz, DMSO-d$_6$) δ 1.74 (d, 3H), 6.40 (m, 1H), 6.52 (br s, 2H), 7.30 (m, 1H), 7.48 (m, 1H), 7.56 (s, 1H); MS m/z 382 (M+1).

4-methanesulfonyloxy-piperidine-1-carboxylic acid tert-butyl ester (2)

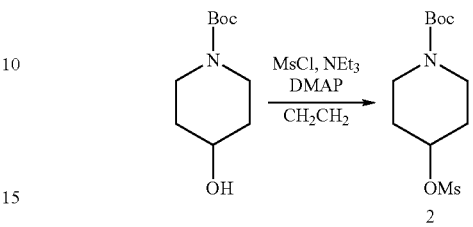

To a stirred solution of 4-hydroxy-piperidine-1-carboxylic acid tert-butyl ester (7.94 g, 39.45 mmol) in CH$_2$Cl$_2$ (100 mL), cooled to 0° C., was slowly added NEt$_3$ (5.54 mL, 39.45 mmol) followed by methane sulfonyl chloride (3.06 mL, 39.45 mmol) and DMAP (48 mg, 0.39 mmol). The mixture was stirred at room temperature overnight. To the mixture was added water (30 mL). Extraction with CH$_2$Cl$_2$ (3×30 mL) followed by drying (Na$_2$SO$_4$) and removal of the solvent in vacuo afforded 4-methanesulfonyloxy-piperidine-1-carboxylic acid tert-butyl ester as a white solid (11.00 g, >99% yield). $^1$H NMR (CDCl$_3$, 400 MHz) δ 4.89 (m, 1H), 3.69 (m, 2H), 3.31 (m, 2H), 3.04 (s, 3H), 1.95 (m, 2H), 1.83 (m, 2H), 1.46 (s, 9H).

tert-butyl-4-[4-(4,4,5,5-tetramethyl-1,32-dioxaborolan-2-yl)-1H-pyrazol-1-yl]piperidine-1-carboxylate

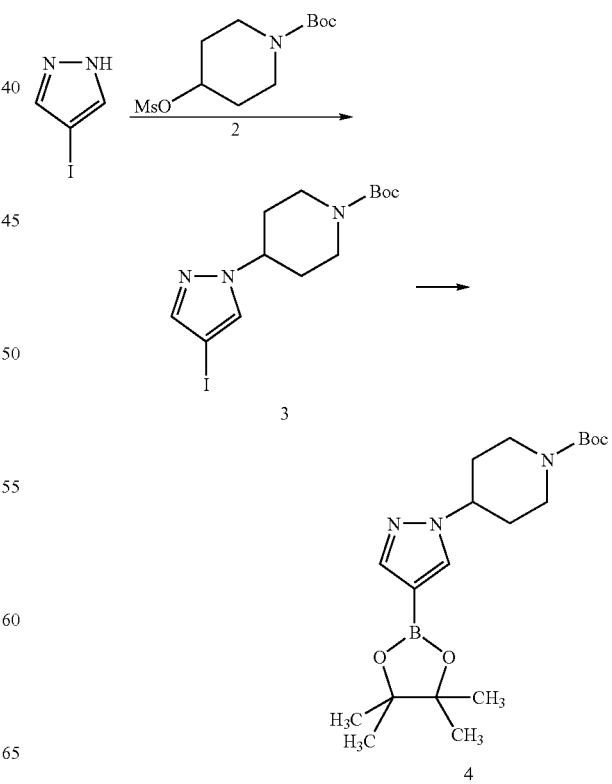

tert-butyl 4-(4-iodo-1H-pyrazol-1-yl)piperidine-1-carboxylate (3)

NaH (1.2 eq., 0.68 mmol) was added portionwise to a stirred solution of 4-iodopyrazole (0.57 mmol) in DMF (2 L) at 4° C. The resulting mixture was stirred for 1 hour at 4° C. and 4-methanesulfonyloxy-piperidine-1-carboxylic acid tert-butyl ester, compound 2 (1.1 eq., 0.63 mmol) was then added. The resulting mixture was heated to 100° C. for 12 h. The reaction was quenched with H₂O and extracted with EtOAc several times. The combined organic layers were dried, filtered, and concentrated to afford an orange oil. The residue was purified by silica gel chromatography (eluting with 5% EtOAc in pentane) to give compound 3 as a white solid (140 g, 66%).

tert-butyl-4-[4-(4,4,5,5-tetramethyl-1,3,2-dioxaborolan-2-yl)-1H-pyrazol-1-yl]piperidine-1-carboxylate (4)

Bis(pinacolato)diboron (1.4 eq., 134 g, 0.52 mol) and potassium acetate (4 eq., 145 g, 1.48 mol) were added sequentially to a solution of compound 3 (140 g, 0.37 mol) in 1.5 L of DMSO. The mixture was purged with nitrogen several times and dichlorobis(triphenylphosphino) palladium (II) (0.05 eq., 12.9 g, 0.018 mol) was then added. The resulting mixture was heated at 80° C. for 2 h. The reaction mixture was cooled to room temperature and filtered through a bed of celite and washed with EtOAc. The filtrate was washed with saturated NaCl (500 mL×2), dried over Na₂SO₄, filtered and concentrated. The residue was purified by silica gel chromatography (eluting with 5% EtOAc in hexanes) to give compound 4 as a white solid (55 g, 40%).

3-[(R)-1-(2,6-dichloro-3-fluoro-phenyl)-ethoxy]-5-(1-piperidin-4-yl-1H-pyrazol-4-yl)-pyridin-2-ylamine (1)

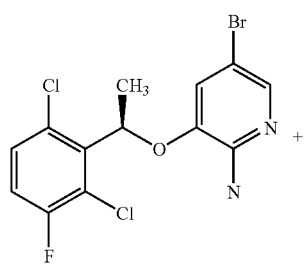

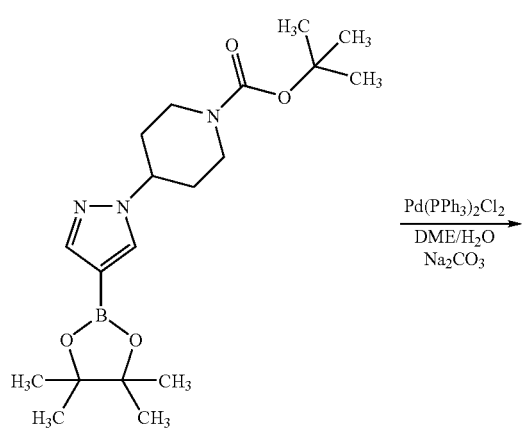

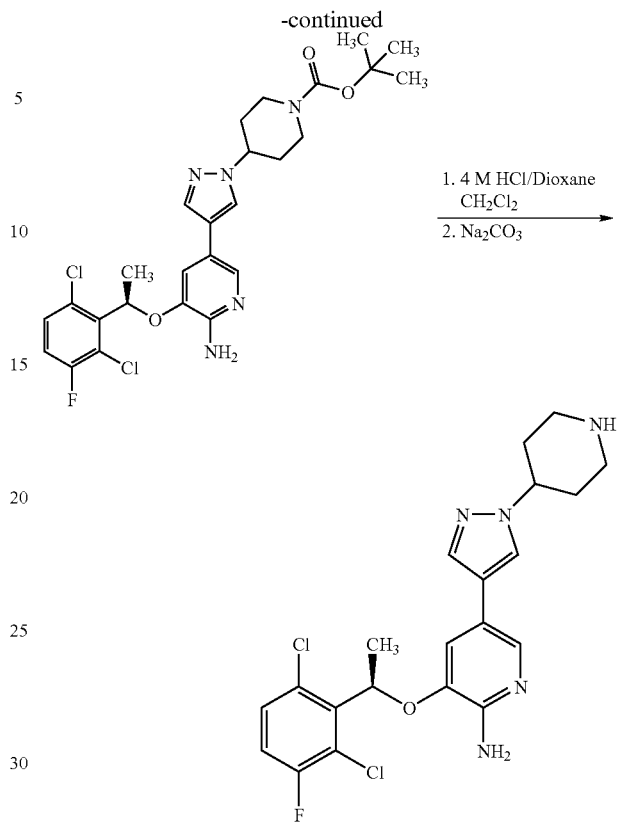

To a stirred solution of 3-[(R)-1-(2,6-dichloro-3-fluoro-phenyl)-ethoxy]-5-(4,4,5,5-tetramethyl-[1,3,2]dioxaborolan-2-yl)-pyridin-2-ylamine (15.22 g, 35.64 mmol) and 4-(4-bromo-pyrazol-1-yl)-piperidine-1-carboxylic acid tert-butyl ester (14.12 g, 42.77 mmol) in DME (143 mL) was added a solution of Na₂CO₃ (11.33 g, 10692 mmol) in water (36 mL). The solution was degassed and charged with nitrogen three times. To the solution was added Pd(PPh₃)₂Cl₂ (1.25 mg, 1.782 mmol). The reaction solution was degassed and charged with nitrogen again three times. The reaction solution was stirred at 87° C. oil bath for about 16 hours (or until consumption of the borane pinacol ester), cooled to ambient temperature and diluted with EtOAc (600 mL). The reaction mixture was filtered through a pad of celite and washed with EtOAc. The EtOAc solution was washed with brine, dried over Na₂SO₄, and concentrated. The crude product was purified on a silica gel column eluting with EtOAc/Hexane system (Biotage 90+Column: equilibrium 600 mL 100% Hexanes, segment 1: 2250 mL 50% EtOAc/Hexanes Linear, segment 2: 4500 mL 75% EtOAc/Hexanes Linear, segment 3: 4500 mL 100% EtOAc) to afford 4-(4-{6-amino-5-[(R)-1-(2, 6-dichloro-3-fluoro-phenyl)-ethoxy]-pyridin-3-yl}-pyrazol-1-yl)-piperidine-1-carboxylic acid tert-butyl ester (11.8 g, 60% yield, ~95% purity) with a Rf of 0.15 (50% EtOAc/Hexanes). MS m/e 550 (M+1)⁺.

To a solution of 4-(4-{6-amino-5-[(R)-1-(2,6-dichloro-3-fluoro-phenyl)-ethoxy]-pyridin-3-yl}-pyrazol-1-yl)-piperidine-1-carboxylic acid tert-butyl ester (11.8 g, 21.45 mmol) in CH₂Cl₂ (59 mL, 0.2M) was added 4N HCl/Dioxane (21 mL). The solution was stirred overnight forming a solid. The solid was crushed thoroughly with a glass rod and sonicated to release starting material trapped in the solid. Additional 4N HCl/Dioxane (21 mL) was added and stirred for another 2 hours at room temperature in which LCMS showed no starting material. The suspension was filtered in a Buchner funnel lined with filter paper. The mother liquor was saved because it contained <5% of product. The solid was transferred to a 500 mL beaker and HPLC water was added until the solid dissolved completely. The pH was adjusted to 10 with the addition of solid $Na_2CO_3$. The water solution was extracted with $CH_2Cl_2$ (5×200 mL) or until LCMS showed no product in the aqueous layer. The $CH_2Cl_2$ solution was dried over $Na_2SO_4$ and concentrated. The crude product, re-dissolved in $CH_2Cl_2$ (10 mL) and MeOH (1 mL), was purified on a silica gel column eluting with $CH_2Cl_2$/MeOH/$NEt_3$ system (Biotage 40+Column: equilibrium 600 mL $CH_2Cl_2$ 100% giving byproduct, segment 1: 1200 mL 10% MeOH/$CH_2Cl_2$ linear, segment 2: 2400 mL 10% MeOH/$CH_2Cl_2$ step, segment 3: 2400 mL 9% MeOH/1% $NEt_3$/$CH_2Cl_2$). The desired fractions were collected to provide 3-[(R)-1-(2,6-dichloro-3-fluoro-phenyl)-ethoxy]-5-(1-piperidin-4-yl-1H-pyrazol-4-yl)-pyridin-2-ylamine (7.19 g, 75% combined yield, white solid). MS m/e 450 (M+1)$^+$. $^1$H NMR (DMSO-$d_6$, 400 MHz) δ 7.92 (s, 1H), 7.76 (s, 1H), 7.58 (m, 1H), 7.53 (s, 1H), 7.45 (m, 1H), 6.90 (s, 1H), 6.10 (m, 1H), 5.55 (bs, 2H), 4.14 (m, 1H), 3.05 (m, 2H), 2.58 (m, 2H), 1.94 (m, 2H), 1.80 (d, 3H), 1.76 (m, 2H).

The solid product 3-[(R)-1-(2,6-dichloro-3-fluoro-phenyl)-ethoxy]-5-(1-piperidin-4-yl-1H-pyrazol-4-yl)-pyridin-2-ylamine was dissolved in dichloromethane, and the solvent was evaporated slowly to generate fine crystalline solid. After high vacuum dry, the sample was confirmed to be a single crystalline polymorph form A with a melting point of 194° C.

We claim:

1. A method of reversing or inhibiting the progress of abnormal cell growth in a mammal comprising, administering to said mammal a therapeutically effective amount of (R)-3-[1-(2,6-dichloro-3-fluoro-phenyl)-ethoxy]-5-(1-piperidin-4-yl-1H-pyrazol-4-yl)-pyridin-2-ylamine or a pharmaceutically acceptable salt thereof, wherein the abnormal cell growth is a cancer mediated by an anaplastic lymphoma kinase.

2. The method of claim 1, wherein the mammal is a human.

3. The method of claim 1, wherein the mammal is a dog.

4. The method of claim 1, wherein the anaplastic lymphoma kinase is a genetically altered anaplastic lymphoma kinase.

5. The method of claim 1, wherein the cancer is selected from the group consisting of non-small cell lung cancer (NSCLC), squamous cell carcinoma, hormone-refractory prostate cancer, papillary renal cell carcinoma, colorectal adenocarcinoma, neuroblastomas, anaplastic large cell lymphoma (ALCL) and gastric cancer.

6. The method of claim 1, wherein (R)-3-[1-(2,6-dichloro-3-fluoro-phenyl)-ethoxy]-5-(1-piperidin-4-yl-1H-pyrazol-4-yl)-pyridin-2-ylamine or pharmaceutically acceptable salt thereof is administered as a pharmaceutical composition comprising (R)-3-[1-(2,6-dichloro-3-fluoro-phenyl)-ethoxy]-5-(1-piperidin-4-yl-1H-pyrazol-4-yl)-pyridin-2-ylamine or a pharmaceutically acceptable salt thereof and at least one pharmaceutically acceptable carrier.

7. The method of claim 2, wherein the anaplastic lymphoma kinase is a genetically altered anaplastic lymphoma kinase.

* * * * *